United States Patent
Gregory et al.

(10) Patent No.: US 7,482,503 B2
(45) Date of Patent: Jan. 27, 2009

(54) WOUND DRESSING AND METHOD FOR CONTROLLING SEVERE, LIFE-THREATENING BLEEDING

(75) Inventors: Kenton W Gregory, 3737 Council Crest, Portland, OR (US) 97201; Simon McCarthy, Portland, OR (US)

(73) Assignees: Providence Health System-Oregon, Portland, OR (US); Kenton W Gregory, Portland, OR (US)

( * ) Notice: Subject to any disclaimer, the term of this patent is extended or adjusted under 35 U.S.C. 154(b) by 475 days.

(21) Appl. No.: 10/480,827

(22) PCT Filed: Jun. 14, 2002

(86) PCT No.: PCT/US02/18757

§ 371 (c)(1),
(2), (4) Date: Oct. 6, 2004

(87) PCT Pub. No.: WO02/102276

PCT Pub. Date: Dec. 27, 2002

(65) Prior Publication Data

US 2005/0038369 A1    Feb. 17, 2005

Related U.S. Application Data

(60) Provisional application No. 60/298,773, filed on Jun. 14, 2001.

(51) Int. Cl.
*A61F 13/00* (2006.01)
*A61L 15/00* (2006.01)
*A01N 43/04* (2006.01)

(52) U.S. Cl. .......................... 602/48; 424/445; 514/55; 536/20

(58) Field of Classification Search .................. 602/48; 424/445, 520, 538; 536/20
See application file for complete search history.

(56) References Cited

U.S. PATENT DOCUMENTS 2,610,625 A    9/1952    Sifferd et al.

(Continued)

FOREIGN PATENT DOCUMENTS

EP    0 353 972 A1 *    2/1990

(Continued)

OTHER PUBLICATIONS

Michele W. Chan et al., "*Comparison of Poly-N-acetyl Glucosamine (P-GlcNAc) with Absorbable Collagen (Actifoam), and Fibrin Sealant (Bolheal) for Achieving Hemostatis in a Swine Model of Splenic Hemorrhage.*"The Journal of Trauma 48(3) pp. 454-458 (2000) Lippincott Williams & Wilkins, Inc. U.S.A.

(Continued)

*Primary Examiner*—Kim M Lewis
(74) *Attorney, Agent, or Firm*—Ryan Kromholz & Manion S.C.

(57) ABSTRACT

This invention is directed to advanced hemorrhage control wound dressings, and methods of using a producing same. The subject wound dressing is constructed from a non-mammalian material for control of severe bleeding. The wound dressing is formed of a biomaterial comprising chitosan for controlling severe bleeding. The kind of severe, life-threatening bleeding contemplated by this invention is typically of the type not capable of being stanched when a conventional gauze wound dressing is applied with conventional pressure to the subject wound. The wound dressing being capable of substantially stanching the flow of the severe life-threatening bleeding from the wound by adhering to the wound site, to seal the wound, to accelerate blood clot formation at the wound site, to reinforce clot information at the wound site and prevent bleed out from the wound site, and to substantially prohibit the flow of blood out of the wound site.

8 Claims, 6 Drawing Sheets

U.S. PATENT DOCUMENTS

| | | | |
|---|---|---|---|
| 2,858,830 A * | 11/1958 | Robins | 604/307 |
| 3,551,556 A | 12/1970 | Kliment et al. | |
| 3,632,754 A | 1/1972 | Balassa | |
| 3,801,675 A | 4/1974 | Russell | |
| 3,849,238 A | 11/1974 | Gould et al. | |
| 3,902,497 A | 9/1975 | Casey | |
| 3,911,116 A | 10/1975 | Balassa | |
| 4,068,757 A | 1/1978 | Casey | |
| 4,195,175 A | 3/1980 | Peniston et al. | |
| 4,394,373 A | 7/1983 | Malette et al. | |
| 4,452,785 A | 6/1984 | Malette et al. | |
| 4,460,642 A | 7/1984 | Errede et al. | |
| 4,501,835 A | 2/1985 | Berke | |
| 4,532,134 A | 7/1985 | Malette et al. | |
| 4,541,426 A | 9/1985 | Webster | |
| 4,772,419 A | 9/1988 | Malson et al. | |
| 4,952,618 A | 8/1990 | Olsen | |
| 4,977,892 A | 12/1990 | Ewall | |
| 5,006,071 A | 4/1991 | Carter | |
| 5,454,719 A | 10/1995 | Hamblen | |
| 5,597,581 A | 1/1997 | Kaessmann et al. | |
| 5,700,476 A | 12/1997 | Rosenthal et al. | |
| 5,756,111 A * | 5/1998 | Yoshikawa et al. | 424/402 |
| 5,836,970 A | 11/1998 | Pandit | |
| 5,858,350 A | 1/1999 | Vournakis et al. | |
| 6,103,369 A | 8/2000 | Lucast et al. | |
| 6,448,462 B2 | 9/2002 | Groitzsch et al. | |
| 6,565,878 B2 | 5/2003 | Schoenfeldt et al. | |
| 6,566,577 B1 | 5/2003 | Addison et al. | |
| 6,693,180 B2 | 2/2004 | Lee et al. | |
| 6,864,245 B2 | 3/2005 | Vournakis et al. | |
| 2002/0071855 A1 | 6/2002 | Sadozai et al. | |
| 2005/0036955 A1 | 2/2005 | DeGould | |
| 2005/0038369 A1 | 2/2005 | Gregory et al. | |
| 2005/0137512 A1 | 6/2005 | Campbell et al. | |

FOREIGN PATENT DOCUMENTS

| WO | WO02/102276 | 12/2002 |
|---|---|---|
| WO | WO03/079946 | 10/2003 |
| WO | WO 03/079946 | 10/2003 |

OTHER PUBLICATIONS

David J. Cole et al., "A pilot study evaluating the efficacy of a fully acetylated ply-N-acetyl glucosamine membrane formulation as a topical hemostatic agent," Surgery 126(3) pp. 510-517 (1999) Mosby, Inc. U.S.A.

Paul A. Sanford et al., "Biomedical Applicants of High-Purity Chitosan," ACS Symposium Series 467 pp. 430-445 (1991) American Chemical Society, Washington D.C.

William G. Malette et al., "Chitosan: A New Hemostatic," The Annals of Thoracic Surgery 36(1) pp. 55-58 (1983).

Roger Olsen et al., "Biomedical Applicants of Chitin and Its Derivatives," Chitin and Chitosan pp. 813-829 (1988) Elsevier Applied Science, London and New York.

Sanford, Paul A.; "Chitosan: Commercial Uses and Potential Applications"; Chitin and Chitosan, Sources, Chemistry, Biochemistry, Physi-cal Properties and Applications; pp. 51-69; 1989.

Paul A. Sanford A., "Biomedical Applications of New Forms of Chitin/Chitosan", Chitin Derivatives in Life Science, 1992.

Sondeen et al, "Comparison of 10 Different Hemostatic Dressings in an Aortic Injury" J Trauma. 2003; 54: 280-285.

Pusateri et al, "Advanced Hemostatic Dressing Development Program: Animal Model Selection Criteria and Re-sults of a Study of Nine Hemostatic Dressings in a Model of Severe Large Venous Hemorrhage and Hepatic Injury in Swine" J Trauma. 2003; 55: 512-526.

HemCon Bandage Training DVD (Photo).

HemCon Bandage Manufacturing Method (Photos and Text).

Wound Dressing Adhesion Testing (Photos and Text).

Wedmore et al, "A Special Report on Chitosan-Based Hemostatic Dressing: Experience in Current Combat Op-erations" J Trauma. 2006; 60: 655-658.

Wislon, "The Army's Greatest Inventions" U.S. Army Materiel Command, 2005 Edition: 30-37.

Portland Business Journal Nov. 4, 2006 "HemCon Bandage Stakes Claim to Soldier's Kit Bag".

Department of the Army: Kevin C. Kiley, M.D., Lieutenant General, The Surgeon General, HemCon® Dressing (HC; chitosan bandage) for Deployed Army Personnel.

Poster Presentation: Horsch et al "Prehospital Use of HemCon Bandage by Paramedics of Mogen David Adom the Israeli National EMS System" May 2007.

Poster Presentation: Belman et al "From the Battlefield to the Street—Experience of a Suburban Fire/EMS Agency with Chitosan Dressing" Aug. 2006.

Siekman, Fortune Small Business, Jul./Aug. 2006: 67-68.

Transcript of CNN Segment Jun. 8, 2006.

* cited by examiner

20mm

20mm    Chitosan Patch

WOUND DRESSING AND METHOD FOR CONTROLLING SEVERE, LIFE-THREATENING BLEEDING

This application claims priority under 35 U.S.C. § 119 Provisional Application No. 60/298,773, filed in the United States on Jun. 14, 2001, the entire contents of which are hereby incorporated by reference.

The U.S. Government has a paid-up license in this invention and the right in limited circumstances to license others on reasonable terms as provided by the terms of Grant No. DAMD17-98-1-8654 awarded by the Army/MRMC—Medical Research and Material Command.

BACKGROUND OF THE INVENTION

An advanced hemorrhage control bandage and methods of its application would substantially augment available hemostatic methods. To date, the application of continuous pressure with gauze bandage remains the preferred primary intervention technique used to stem blood flow, especially that from severely bleeding wounds. However, this procedure neither effectively nor safely stanches severe blood flow. This has been, and continues to be, a major survival problem in the case of severe life-threatening bleeding from a wound.

Furthermore, it is widely accepted that severe bleeding is the leading cause of death from wounds on the battlefield, accounting for approximately 50 percent of such deaths. It is estimated that one-third of these deaths may be preventable with enhanced hemorrhage control methods and devices. Such enhanced hemorrhage control would also prove most useful in the civilian population where hemorrhage is the second leading cause of death following trauma.

Currently available hemostatic bandages, restricted to use in surgical applications, such as collagen wound dressings or dry fibrin thrombin wound dressings are not sufficiently resistant to dissolution in high blood flow nor do they have strong enough adhesive properties to serve any practical purpose in the stanching of severe blood flow. These currently available surgical hemostatic bandages are also delicate and thus prone to failure should they be damaged by bending or loading with pressure.

There is prior art relating to chitosan and chitosan dressings. For example, U.S. Pat. No. 4,394,373 employs chitosan in liquid or powder form to agglutinate blood in microgram/ml quantities. Also, U.S. Pat. No. 4,452,785 is directed to a method of occluding blood vessels therapeutically by injecting chitosan directly into the vessels. U.S. Pat. No. 4,532,134 further relates to hemostatis, inhibiting fibroplasias, and promoting tissue regeneration by placing in contact with the tissue wound a chitosan solution or water-soluble chitosan. The chitosan forms a coagulum which prevents bleeding.

Moreover, U.S. Pat. No. 5,858,350 relates to a process to make diatom derived biomedical grade, high purity chitin and chitin derivatives (so called protein-free even though this is not demonstrated by analysis in the patent). The proposed advantage of so called protein-free chitin/chitosan materials are that they should be significantly less antigenic than current shrimp and crab derived chitin materials.

Mi, F L, et al, *Fabrication and Characterization of a Sponge-Like Assymetric Chitosan Membrane as a Wound Dressing,* Biomaterials, 22(2):165-173 (2001) describes the fabrication and wound healing function of an asymmetric chitosan membrane produced by a phase inversion method.

Chan, M W, et al, *Comparison of Poly-N-acetyl Glucosamine (P-GlcNAc) with Absorbable Collagen (Actifoam), and Fibrin Sealant (Bolheal) for Achieving Hemostasis in a Swine Model of Splenic Hemorrhage,* J. Trauma, Injury, Infection, and Critical Care, 48(3):454-458 (2000) describes the testing of chitin/chitosan hemostatic patches under the moderate blood flow and oozing typical of the swine spleen capsular stripping test.

Cole, D. J., et al, *A Pilot Study Evaluating the Efficacy of a Fully Acetylated poly-N-acetyl glucosamine Membrane Formulation as a Topical Hemostatic Agent,* Surgery 126(3):510: 517 (1999) describes hemostatic agent testing in the swine spleen capsular stripping test.

Sandford, Steinnes A., *"Biomedical Applications of High Purity Chitosan" in Water Soluble Polymers, Synthesis, Solution Properties and Applications,* ACS Series 467, Shalaby W S. McCormick C L. Butler G B. Eds. ACS, Washington, D.C. 1991, Ch 28, 431-445. This is a general review paper describing chitosan use with reference to a chitosan sponge.

Mallette, W. G., et al, Chitosan: A New Hemostat, The Annals of Thoracic Surgery, 36(1), 55-58, (1983) See comments concerning the Malette patents above.

Olsen, R., et al, In Chitin and Chitosan, Sources, Chemistry, Biochemistry, Physical Properties and Applications, Elsevier Applied Science, London and New York, 1989, 813-828. This paper concerns the agglutinating efficiency of chitosan.

Japanese Patent 60142927 covers a chitosan medical band with improved tack Japanese patent 63090507 A2 describes a water insoluble and 2% acetic acid insoluble chitosan sponge for external hemostatic application or for protection of a wound.

U.S. Pat. No. 5,700,476 describes collagen based structurally inhomogeneous sponges for wound dressings and/or implant applications formed by freeze drying techniques employing at least one pharmacological agent and at least one substructure.

U.S. Pat. No. 2,610,625 relates to freeze dried sponge structures that are highly effective in stopping the flow of blood or other fluids and which will be absorbed after a time in the body. This patent describes collagen sponge preparation.

U.S. Pat. No. 5,836,970 comprises a wound dressing formed of a blend or mixture of chitosan and alginate.

SUMMARY OF THE INVENTION

The invention is directed to a first-aid/primary intervention wound dressing for control of severe, life-threateninncg bleeding. The subject wound dressing is typically relatively low cost. Presently there are no low cost wound dressings that address or any wound dressings that are suitable for control of severe life-threatening bleeding. Such bleeding can be fatal in ballistic injuries and severe arterial lacerations. There is an urgent need for this type of dressing especially in the battlefield where typically 50% of all deaths are associated with an inability to immediately control severe bleeding.

An advanced wound dressing for control of severe, life-threatening bleeding should preferably have the following properties:

i) easily and quickly applied in one step after removal from package ii) rapid and strong blood clotting iii) rapid and strong tissue adhesion iv) strong internal cohesive properties v) rapid and strong wound sealing vi) resistant to dissolution under strong blood flow vii) able to be treated roughly without compromising efficacy This invention is directed to advanced hemorrhage control wound dressings, and methods of using and producing same. The subject wound dressing is constructed from a non-mammalian material for control of severe bleeding. The preferred non-mammalian material is poly [β-(1→4)-2-amino-2-deoxy-D-glucopyranose] more commonly referred to as chitosan.

In general, the subject dressing is formed of a biomaterial comprising chitosan for controlling severe bleeding. Preferably, the biomaterial comprises a non-mammalian material. The kind of severe, life-threatening bleeding contemplated by this invention is typically of the type not capable of being stanched when a conventional gauze wound dressing is applied with conventional pressure to the subject wound. Alternatively, the nature of the severe, life-threatening bleeding is such that it is not capable of being stanched when a conventional gauze wound dressing is applied with conventional pressure to the wound and, if not controlled by other means, would result in the person lapsing into a state of hypotension. Stated another way, the severe, life-threatening bleeding is generally not capable of being stanched when a conventional gauze wound dressing is applied with conventional pressure to the wound and, if not controlled by other means, would result in the systolic blood pressure of the person dropping to a level of less than about 90 mm Hg.

The severe, life-threatening bleeding can also be described as a steady high flow of blood of more than about 90 ml of blood loss per minute, such that in about 20 minutes of bleeding a volume of more than about 40% of total blood from a 70 kg human male would be lost, and the blood volume loss would substantially reduce the likelihood of survival of the person. In many cases, the severe bleeding is caused by a ballistic projectile injury or a sharp perforation injury or a blunt traumatic injury. In other cases, the severe bleeding is caused by coagulopathy or internal trauma or surgical trauma.

The wound dressing is preferably capable of stanching said severe bleeding which is caused by a substantial arterial wound or a substantial venous wound having a blood flow rate of at least about 90 ml/minute. The wound dressing is also preferably capable of adhering to the wound site by the application of direct pressure to the wound dressing for a period of time of not more than about five minutes. The wound dressing also preferably acts quickly to seal the wound. The wound dressing also preferably facilitates substantial clotting and agglutinating of the severe bleeding from the wound site, and stanches the severe bleeding with the temporary application of direct pressure to the wound dressing. The wound dressing preferably has a high resistance to dissolution in high blood flow. The wound dressing preferably has good internal cohesion properties and thus has sufficient flexibility and toughness to resist rough handling.

The wound dressing is typically produced from a chitosan biomaterial and formed into a sponge-like or woven configuration via the use of an intermediate structure or form producing steps. Such structure or form producing steps are typically carried out from solution and can be accomplished employing techniques such as freezing (to cause phase separation), non-solvent die extrusion (to produce a filament), electro-spinning (to produce a filament), phase inversion and precipitation with a non-solvent (as is typically used to produce dialysis and filter membranes) or solution coating onto a preformed sponge-like or woven product. In the case of freezing, where two or more distinct phases are formed by freezing (typically water freezing into ice with differentiation of the chitosan biomaterial into a separate solid phase), another step is required to remove the frozen solvent (typically ice), and hence produce the wound dressing without disturbing the frozen structure. This can be accomplished by a freeze-drying and/or a freeze substitution step. The filament can be formed into a non-woven sponge-like mesh by non-woven spinning processes. Alternately, the filament can be produced into a felted weave by conventional spinning and weaving processes. Other processes that may be used to make the said biomaterial sponge-like product include dissolution of added porogens from a solid chitosan matrix or boring of material from said matrix.

The wound dressing is preferably formed of a biomaterial comprising an interconnected open porous structure, and/or an oriented open lamella structure, and/or an open tubular structure, and/or an open honeycomb structure, and/or a filamentous structure. The wound dressing has interconnected free-space domains or pores with pore diameters of preferably at least about 15 microns, more preferably at least about 30 microns, most preferably at least about 35 microns, preferably up to about 100 microns, more preferably up to about 125 microns, and most preferably up to about 150 microns.

The wound dressing has an available blood contacting surface area per base surface of said wound dressing of preferably at least about 100 cm$^2$ per cm$^2$, more preferably at least about 200 cm$^2$ per gram per cm$^2$, and most preferably at least about 300 cm$^2$ per gram per cm$^2$. The available mass of chitosan biomaterial per wound surface area is preferably at least about 0.02 g/cm$^2$, more preferably at least about 0.04 g/cm$^2$, and most preferably at least about 0.06 g/cm$^2$.

Furthermore, the wound dressing has a mean rate of dissolution per base surface area of said wound dressing when adhered to said wound site, at a temperature of about 37° C., of preferably not more than about 0.008 grams per minute per cm$^2$, more preferably not more than about 0.005 grams per minute per cm$^2$, and most preferably not more than about 0.002 grams per minute per cm$^2$.

The subject wound dressing preferably has a density of at least about 0.05 g/cm$^3$, more preferably at least about 0.07 g/cm$^3$, and most preferably at least about 0.11 g/cm$^3$. It can have a compression loading preferably to a compression density at least about 0.05 g/cm$^3$, more preferably at least about 0.07 g/cm$^3$, most preferably at least about 0.095 g/cm$^3$, and preferably of not more than about 0.14 g/cm$^3$, more preferably not more than about 0.12 g/cm$^3$, most preferably not more than about 0.10 g/cm$^3$.

A wound dressing of this invention typically contains chitosan with number average molecular weight of at least about 50 kda, preferably at least about 75 kda, more preferably at least about 100 kda, and most preferably at least about 150 kda (molecular weights determined by Gel Permeation Chromatography relative to polyethylene glycol standards in pH 5.5, 0.01 M sodium acetate). The chitosan also preferably has a weight average molecular weight of at least about 100 kda, more preferably at least about 150 kda, and most preferably at least about 300 kda (molecular weights determined by Gel Permeation Chromatography relative to polyethylene glycol standards in pH 5.5, 0.01 M sodium acetate). The chitosan in the wound dressing also has a Brookfield LV DV-II+ viscosity at 25° C. in 1% solution and 1% acetic acid (AA) with spindle LV1 at 30 rpm which is preferably not less than 100 centipoise, more preferably not less than 125 centipoise, most preferably not less than 150 centipoise, The molecular weights and viscosities referred to immediately above are in respect to substantially pure chitosan wound dressings and wound dressings formed with an adsorbed surface layer of chitosan. In the case of a wound dressing containing a covalently bound surface layer of chitosan, then lower viscosities and molecular weights of chitosan may be preferred.

The wound dressing of the present invention can comprise cationic chitosan salts for promoting tissue adhesion and tissue sealing. Preferably, the cationic chitosan salts are selected from a group consisting of chitosan formate, chitosan acetate, chitosan lactate, chitosan ascorbate and chitosan citrate. The chitosan has a degree of deacetylation which is typically at least about 70%, preferably at least about 75%, more preferably at least about 80%, most preferably at least about 85%.

In a preferred form of this invention, the wound dressing has a backing support layer attached thereto that provides for and that facilitates improved handling and mechanical properties. This backing layer can be attached or bonded to the dressing by direct adhesion with the top layer of chitosan, or an adhesive such as 3M 9942 acrylate skin adhesive, or fibrin glue or cyanoacrylate glue can be employed. This backing support layer is also preferably substantially blood insoluble. The backing support layer is also preferably substantially blood impermeable. The backing support layer is also preferably substantially biodegradable. The backing support layer is preferably a material which allows for firm handling of the bandage during application and non-sticking to hands once bandage has been applied.

Preferably, the material which forms the backing support layer is a layer of polymeric material. Examples of preferred backing materials include low-modulus meshes and/or films and/or weaves of synthetic and naturally occurring polymers. Synthetic biodegradable materials include poly(glycolic acid), poly(lactic acid), poly(e-caprolactone), poly($\beta$-hydroxybutyric acid), poly($\beta$-hydroxyvaleric acid), polydioxanone, poly(ethylene terephthalate), poly(malic acid), poly(tartronic acid), polyphosphazene and the copolymers of the monomers used to synthesize the above-mentioned polymers. Naturally occurring biodegradable polymers include chitin, algin, starch, dextran, collagen and albumen. Non-biodegradable polymers for temporary external wound applications include polyethylene, polypropylene, metallocene polymers, polyurethanes, polyvinylchloride polymers, polyesters and polyamides.

The wound dressing of this invention has the degree of adhesion to the wound site which is preferably at least about 40 kPa, more preferably at least about 60 kPa, and most preferably at least about 100 kPa. Also, the wound dressing has a thickness which is preferably not less than about 3.0 mm, more preferably not less than about 3.5 mm, and most preferably not less than about 4.0 mm, and preferably not more than about 8.0 mm, more preferably not more than about 7.0 mm, and most preferably not more than about 6.5 mm.

A wound dressing (2.5 cm wide) of this invention preferably has an ultimate tensile breaking load of not less than 1 kg, more preferably at least 1.5 kg and most preferably at least 2.25 kg. This same dressing preferably has an ultimate elongation of at least 70%, more preferably at least 90% and most preferably at least 110%. The young's modulus of this dressing is preferably less than 5 MPa, more preferably less than 3 MPa and most preferably less than 1 MPa.

The wound dressing preferably includes a supplemental traction surface which is particularly useful for the application of the wound dressing to a wound site which includes a significant amount of surface blood. The supplemental traction surface can comprise at least one outer surface which grips the wound site to avoid slipping of wound dressing, typically in a direction away from the wound site, during use. The supplemental traction surface is preferably in the form of a tread design.

The subject wound dressing is preferably capable of forming an adhesive material in combination with blood flowing from said wound at the wound dressing-blood interface. In this case, the adhesive material preferably has a pH of not more than about 5.5, more preferably not more than about 4.5, more preferably not more than about 4, when the wound is sealed. Typical acids employed for purposes of adjusting the pH of the wound dressing are as follows: acetic acid, formic acid, lactic acid, ascorbic acid, hydrochloric acid and citric acid. The mole ratio of acid anion to glucosamine functional groups in the chitosan cation/anion pair to adjust the pH to the level described above is preferably about 0.90, more preferably about 0.75, and most preferably about 0.60.

The wound dressing is preferably capable of being conformed to the configuration of the wound, for engagingly contacting the wound, and for facilitating stanching of the flow of the severe life-threatening bleeding. More particularly, the wound dressing is introduced into the interstices of the wound. More preferably, the wound dressing is capable of being conformed into a tubular configuration. Then, the reconfigured wound dressing is inserted into the wound.

This invention also contemplates a method for controlling severe, life-threatening bleeding from a wound at a wound site of a person. The method comprises providing a wound dressing formed of a biomaterial comprising chitosan, adhering said wound dressing to the wound site and substantially stanching the flow of said severe life-threatening bleeding from said wound. Preferably, the wound is sealed and bleed out is prevented from said wound site. Also, bleeding and the flow of other fluids into and/or out of the said wound site are preferably prevented.

It has been found that the dressing typically acts to rapidly produce a strong clot at the bleeding site by agglutinating red blood cels. It can also promote clotting by accelerating the normal platelet clotting pathway.

A method can also be provided for producing a wound dressing capable of controlling severe, life-threatening bleeding from a wound at a wound site of a person. Such a method comprises the steps of providing a chitosan biomaterial as described above.

Preferably, the chitosan biomaterial is degassed. Typically, degassing is removing sufficient residual gas from the chitosan biomaterial so that, on undergoing a subsequent freezing operation, the gas does not escape and form unwanted voids or trapped gas bubbles in the subject wound dressing product. The degassing step can be performed by heating a chitosan biomaterial, typically in the form of a solution, and then applying a vacuum thereto. For example, degassing can be performed by heating a chitosan solution to 60° C. immediately prior to applying vacuum at 500 mTorr for 5 minutes while agitating the solution.

Next, the chitosan biomaterial, which is typically in solution form, is subjected to a freezing step. Freezing is preferably carried out by cooling the chitosan biomaterial solution and lowering the solution temperature from room temperature to a final temperature below the freezing point. In this way, the preferred structure of the wound-dressing product can be prepared. The final freezing temperature is preferably not more than about −10° C., more preferably not more than about −20° C., and most preferably not more than about −30° C. Preferably, the temperature is gradually lowered over a predetermined time period. For example, the freezing temperature of a chitosan biomaterial solution can be lowered from room temperature to −45° C. by application of a constant temperature cooling ramp of between −0.4° C./min to −0.8° C./min for a period of 90 minutes to 160 minutes.

Preferably, the frozen chitosan biomaterial then undergoes water removal from within the interstices of the frozen material. This water removal step can be achieved without damaging the structural integrity of the frozen chitosan biomaterial. Typically, this is achieved without producing a substantial liquid phase which can disrupt the structural arrangement of the ultimate wound dressing. Thus, preferably, the chitosan biomaterial passes from a solid frozen phase into a gas phase without the substantial formation of an intermediate liquid phase.

The preferred manner of implementing water removal is by employing a freeze-drying step. Freeze-drying of the frozen chitosan biomaterial can be conducted by further freezing the frozen chitosan biomaterial. Typically, a vacuum is then applied thereto. Next, it is preferred to heat the evacuated frozen chitosan material. Then, there can be a preferred step of drying the heated, evacuated, frozen chitosan material.

More specifically, the frozen chitosan biomaterial can be subjected to subsequent freezing preferably at about −15° C., more preferably at about −25° C., and most preferably at about −45° C., for a preferred time period of at least about 1 hour, more preferably at least about 2 hour, and most preferably at least about 3 hour. This can be followed by cooling of the condenser to a temperature of less than about −45° C., more preferably at about −60° C., and most preferably at about −85° C. Next, a vacuum in the amount of preferably at most about 150 mTorr, more preferably at most about 100 mTorr, and most preferably at least about 50 mTorr, can be applied. Then, the evacuated frozen chitosan material can be heated preferably at about −25° C., more preferably at about −15° C., and most preferably at about −10° C., for a preferred time period of at least about 1 hour, more preferably at least about 5 hour, and most preferably at least about 10 hour. Finally drying can be conducted at preferably at a temperature of about 20° C., more preferably at about 15° C., and most preferably at about 10° C., for a preferred time period of at least about 36 hour, more preferably at least about 42 hour, and most preferably at least about 48 hour.

Subsequently, the chitosan biomaterial as previously treated can be compressed, such as by using heated platens, to reduce the thickness and increase the density of said wound dressing. The compression temperature is preferably not less than 60° C., more preferably it is not less than 75° C. and not more than 85° C. Then, the pressed chitosan biomaterial is preferably preconditioned by heating same to a temperature of preferably up to about 75° C., more preferably to a temperature of up to about 80° C., and most preferably to a temperature of preferably up to about 85° C. Preconditioning is typically conducted for a period of time up to about 0.25 hours, preferably up to about 0.35 hours, more preferably up to about 0.45 hours, and most preferably up to about 0.50 hours, thereby increasing the adhesion strength and dissolution resistance of said wound dressing, as previously described above.

The processed wound dressing can then be subjected to a sterilization step. The dressing can be sterilized by a number of methods. For example, a preferred method is by irradiation, such as by gamma irradiation, which can further enhance the blood dissolution resistance, the tensile properties and the adhesion properties of the wound dressing. The irradiation can be conducted at a level of at least about 5 kGy, more preferably a least about 10 kGy, and most preferably at least about 15 kGy. The sterilized wound dressing can be subsequently packaged for storage in a heat sealed pouch purged with an inert gas such as either argon or nitrogen gas.

A wound dressing is produced from said chitosan biomaterial which is capable of substantially stanching the flow of severe life-threatening bleeding from a wound by adhering the wound dressing to the wound site. The wound dressing is preferably sealed to said wound and prevents bleed out from said wound site by adhering said wound dressing to said wound site employing clotting and agglutinating of the severe bleeding. This wound dressing preferably adheres strongly to the wound site, while clotting and agglutinating red blood cells from around the wound, so that pressure need only be employed preferably in the first five minutes of application. In one form of this invention, the device is designed to be a temporary dressing which is applied, even by unskilled practitioners, in order to keep the wounded person alive until expert medical intervention is possible.

In certain applications, the dissolution rate of the subject wound dressing has been relatively slow compared to the agglutination rate, and this balance has produced good results (agglutination at high enough rate stops dissolution). Also it has demonstrated the importance of uniformity of the internal and surface structure of the wound dressing. If a substantial defect is present in the wound dressing, such as a channel caused by grain boundaries or minor cracking, then significant blood flow will channel its way along the defect and produce a highly undesirable bleed-through condition which can flush away the smaller less-viscous agglutination areas as they form. Also significant blood flow at pressure over the wafer surface appears to adversely affect wound adhesion of prior art wound dressing, but not the wound adhesion of the wound dressing of this invention.

An important preferred attribute of this wound dressing herein is the means of combining the chitosan with the blood while achieving good mechanical integrity of the resultant "clot" and good binding of the clot to the surface immediately adjacent to the injury. The subject wound dressing preferably accelerates blood clot formation at the wound site, to reinforce clot formation at the wound site and prevent bleed out from the wound site, and to substantially prohibit the flow of blood and other fluids into and/or out of the wound site.

The wound dressing of the present invention maintains it's extraordinary dual capability for clotting and adhesion to a wound site, as described above, while at the same time exhibiting a high level of resilience in an extreme environment. The exceptional resilience of this wound dressing is exemplified by the formidable physical properties thereof which are described herein. The subject wound dressing, unlike prior art products described above, also has an outstanding ability to conform to wound shape while maintaining structural resilience. This structural resilience is a capacity for the wound dressing to assume a preferred shape after deformation without any substantial loss of mechanical properties.

The subject wound dressing, unlike prior art product described above, also has excellent structural memory. Structural memory comprehends the capacity of the wound dressing to substantially restore its previous shape after deformation.

DETAILED DESCRIPTION OF PREFERRED EMBODIMENTS

Table 1 provides a list of the main chitosan materials acquired for hemorrhage control testing. With the exception of the Gelfoam™+thrombin, and Surgicel™ controls for swine spleen experiments and the Johnson and Johnson 4"×4" gauze control for use in swine aortic perforations, the dressing materials were all chitosan-based.

Aqueous solutions (2.00% w/w) were prepared in clean, sterile, 1 liter Pyrex flasks from Ametek UF water and dry chitosan. In the case of the Carbomer, Primex and Genis chitosan materials, 1.0% or 2.0% w/w of glacial acetic acid (Aldrich 99.99%) was added to the aqueous mixtures. Dissolution was achieved by shaking of the flask at 40° C. for 12 to 48 hours. The solutions were degassed by application of vacuum at 500 mTorr at room temperature immediately prior to freezing.

Figure 1:
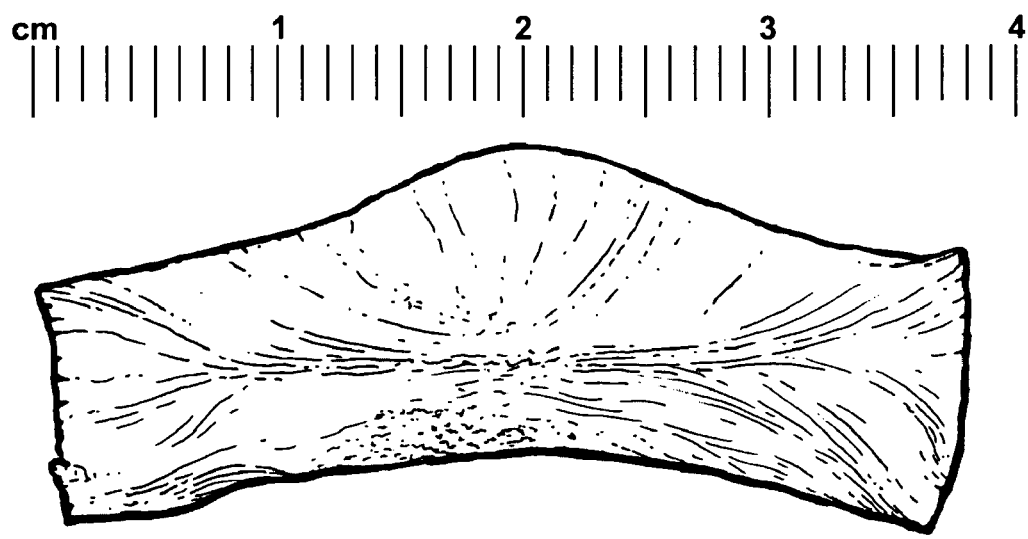
FIG. 1. Photo-digital image of transverse cross section through early uncompressed wound dressing.
Figure 2:
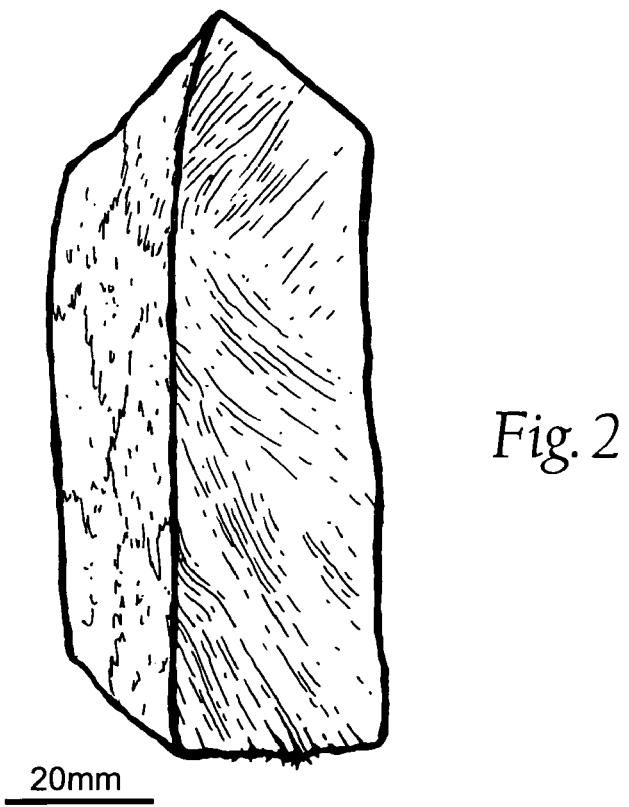
FIG. 2. Photo-digital image of transverse cross section through oriented lamella structures in uncompressed wound dressing.
Figure 3:
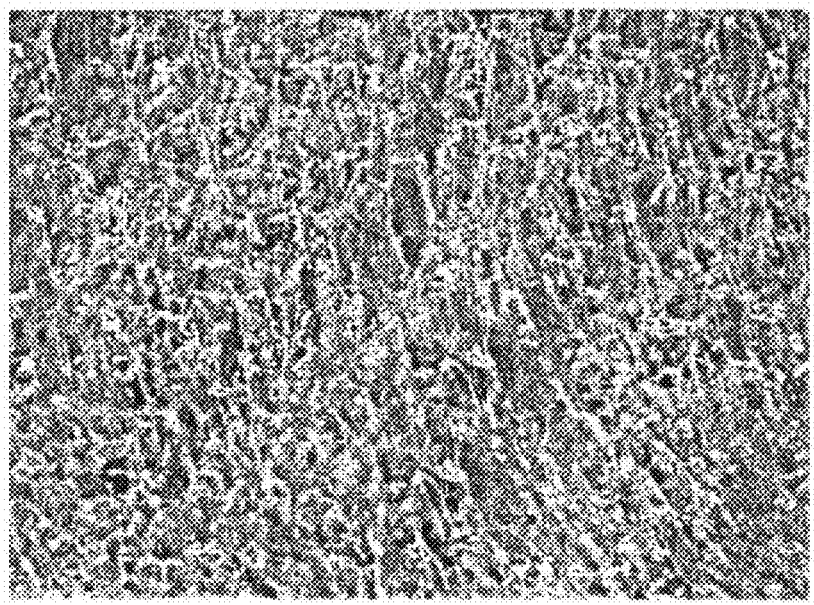
FIG. 3. Light photomicrograph of interconnected porous chitosan wound dressing structure sectioned normal to base FIG. 4. Photograph of chitosan biomaterial wound dressing after heating and compression.
Figure 5:
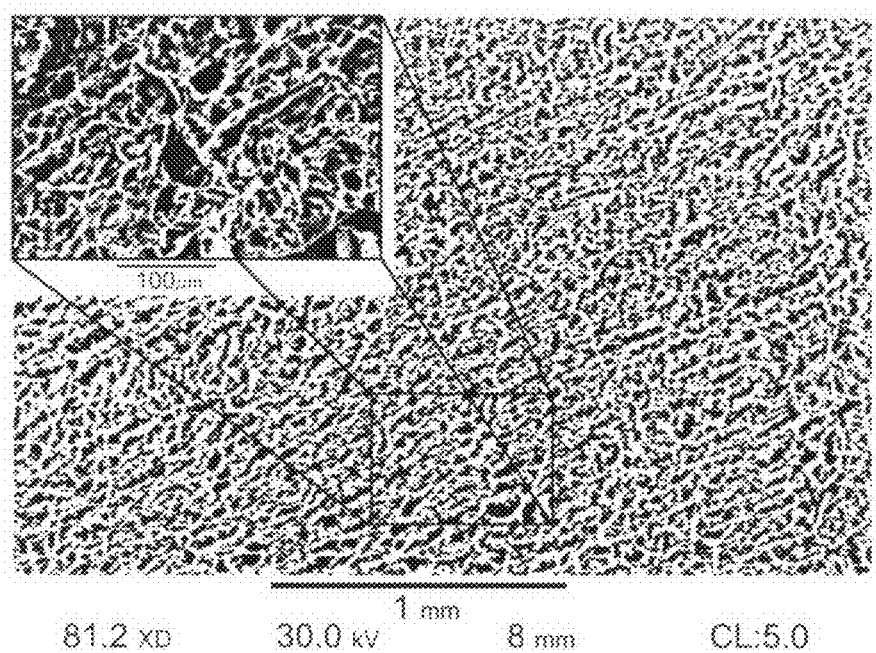
FIG. 5. Scanning electron photomicrographs of a typical base surface of compressed chitosan wound dressing. Higher magnification inset (bar=100 micron).

Wound dressings were prepared from the 2% aqueous solutions of chitosan that were poured into Teflon™-coated aluminum or polystyrene molds to at least 1.5 cm deep and frozen in a −80° C. Revco freezer at −45° C. for 3 hours. Alternatively, freezing was carried out on the shelves inside a Virtis Genesis 35EL freeze drier. There was at most 10% shrinkage in the wound dressings and the final freeze-dried wound dressing density was near 0.033 g/cm$^3$. Transverse cross sections of two types of molded wound dressings are shown in FIGS. 1 & 2 (different freezing rates). The structures observed (see also FIG. 3) were affected by the rates of cooling in the bulk solution and at the different surfaces. Subsequently, structures in the wound dressings were controlled by formulation, mold (size & shape) and freezing conditions. Optimal wound dressing structures were those that were open-porous consisting of uniform interconnected pores of close to 50 microns in diameter or lamella and hexagonal structures normal to the plane of cooling, These structures could be controlled, yielding flexible yet strong wound dressings of large specific surface areas for highly efficient and rapid blood coagulation. Typically the available specific surface area for such structures were greater than 500 cm$^2$/g. The scanning electron photomicrograph in FIG. 5 shows the typical open cell structure in the base surface of a wound dressing. The wound dressings were heated in a convection oven at 80±1° C. for one half hour to optimize the structure and distribution of acetic acid concentration. It was found that this step was essential to optimize the adhesive properties of the wound dressing in a bleeding field (typically adhesion to dermis>40 kPa).

Figure 4:
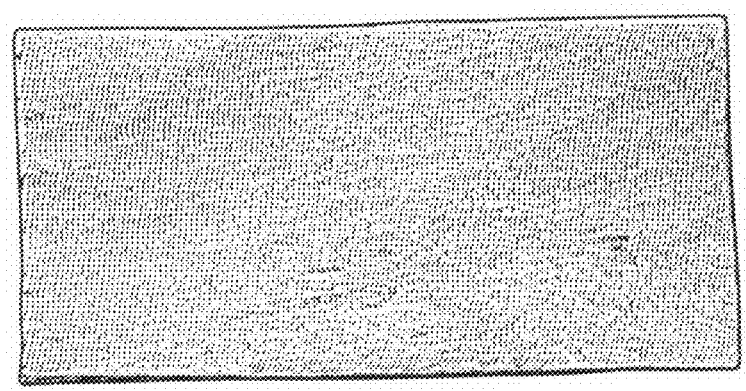

The wound dressings were immediately compressed from 17 mm thickness to 5.5±0.5 mm at 80±5° C. under a loading of close to 50 kPa. (from ca. density 0.03±0.005 g/cm$^3$ to 0.12±0.02 g/cm$^3$). FIG. 4 shows the appearance of the base of a typical preferred chitosan wound dressing for hemorrhage control after heating and compression.

A preferred method preparation of hemostatic wound dressings is as follows:

a) Dry chitosan powder or flake with degree of deactylation above 85%, less than 26 ppm metallic component and greater than 90% dry solids content was made into a 2% aqueous solution (w/w) with 2 or 1% acetic acid (w/w) at 40° C.

b) The solution of chitosan from a) above was degassed under reduced pressure at up to 500 mTorr under agitation for at least 5 minutes and poured into a mold to a depth of 1.7 cm. Certain low-density, foam structures exhibited problems due to their ready dissolution in a bleeding field. These problems were generally avoided by thorough degassing of the solution.

c) The mould containing the degassed chitosan solution was frozen by cooling from room temperature to −45° C. A linear cooling ramp was used over a 90 minute period, and the temperature was maintained at −45° C. for at least another hour.

d) The frozen chitosan was then freeze dried using a condenser which was at a temperature below −70° C. and a vacuum at about 100 mTorr. The shelf temperature was ramped from −45° C. to −15° C. and held at that level for 10 hours. A further 36-48 hours of freeze drying at 10° C. was then performed. Freeze drying was performed until achieving close to about 2.8% of the original frozen plaque mass.

e) At 2.8% of original mass, the process was stopped and the freeze dried wound dressing removed from the mold.

f) The product formed was an acid buffered, water soluble, high specific surface area wound dressing that had shrunk 10% from its original frozen volume. The wound dressing structure was generally a uniform open porous structure with 50 to 80 micron diameter interconnecting pores. Using a slightly different cooling regime in which supercooling was not affected, a lamella/hexagonal structure (with uniformly thin chitosan sheets close to 5 microns thick with close to 50 microns separation between sheets) was achieved.

g) The wound dressing was then compressed (from 1.7 cm to ca. 0.5 cm thick) between smooth and flat platens heated to 80±2° C. under application of 60±20 kPa pressure.

h) Next, the dressing was conditioned in a convection oven by heating at 80±5° C. for 30 minutes.

i) Each wound dressing was then stored in labeled Kapak 530 heat sealed pouches.

j) The resultant pressed wound dressing was tough, flexible, hemostatic, adherent to wet tissue and resistant to dissolution by streaming blood.

k) Improved dissolution properties, improved adhesion strength and sterilization were achieved by exposure of the wound dressing to 15 kGy gamma irradiation under nitrogen atmosphere.

TABLE 1

| Source | Protosan (Norway) | | | | Carbomer (USA) | | Primex (Norway) | | | Genis (Iceland) |
|---|---|---|---|---|---|---|---|---|---|---|
| Sample Name | G213 | G113 | CL213 | CL113 | 9012-75-4 | | Chitoclear | | | |
| Batch Number | 511-583-01 | 005-370-01 | 607-783-02 | 310-490-01 | VA-UY992 | BN 381 | TM 752 | TM 751 | | SO11115-1 |
| Bio-Source | Crab &/or Shrimp | Crab &/or Shrimp | Crab &/or Shrimp | Crab &/or Shrimp | Shrimp | Shrimp | Shrimp | Shrimp | | Shrimp |
| Appearance | Fine white powder | Fine white powder | Fine white powder | Fine white powder | Yellowed powder + specks | Fine off-white powder | Fine off-white powder | Fine off-white powder | | Off-white flake |
| Viscosity cps (1% soln) | 108 | 12 | 133 | 12 | NA | NA | 109 | 156 | | 1216 |
| % Dry Matter | 93.0 | 90.3 | 90.8 | 93.9 | NA | NA | 97.7 | 97.6 | | 93 |
| % Protein | 0.2 | 0.2 | 0.1 | 0.1 | NA | NA | <0.3% | <0.3% | | <0.3% |
| % Deacetylation | 86 | 85 | 84 | 87 | 90 | 89 | 93 | 91 | | 90 |
| Low Metals* | Yes | Yes | Yes | Yes | Yes | Yes | Yes | Yes | | Yes |
| Salt | Glutamate | Glutamate | Chloride | Chloride | Non salt | Non salt | Non salt | Non salt | | Non salt |

*Below accepted limits of lead, mercury, bismuth, antimony, tin, cadmium, silver, copper and molybdenum.
NA = not available.

In vivo evaluation of hemostasis of candidate hemorrhage control dressings of varying composition and structure was screened in increasingly challenging animal models of hemorrhage as hereinafter described. A spleen laceration model was utilized in order to be able to screen large numbers of candidate dressings in a simple reproducible model and to compare them to conventional materials. Although this is the least challenging bleeding model (mild oozing bleeding ca. 2-5 ml/min), most initial wound dressing formulations failed this test. Also all chitosan gels, powders failed in this test while films performed poorly.

Prior to testing in a severe hemorrhage model, swine were anticoagulated with systemic intravenous heparin and better materials were tested in a capsulated spleen stripping model (strong oozing bleeding ca. 10-20 ml/min). Those few materials that passed this test were then evaluated in the carotid laceration model (ca. 50 ml/min) in anticoagulated swine. Wound dressing formulations of candidate materials passing this test were then tested on the swine aortotomy model with in which 4 mm diameter perforations in were made in the thoracic or abdominal aortas. Materials passing these challenging models of severe vascular hemorrhage (bleeding rates in excess of 100 ml/min) were also tested in a severe (Grade V) model of hepatic trauma.

The testing described here was carried out on healthy animals that had previously undergone procedures and were scheduled to be sacrificed for evaluation. All experiments were performed in accordance with the 1996 Nation Research Council, "Guide for the Care and Use of Laboratory Animal" and applicable Federal regulations. After identification of the animal, anesthesia was induced with Telazol 4-9 mg/kg I/M. Isoflurane was given by mask and the animal was intubated.

The chitosan patches for the laceration and capsular stripping experiments were either equal size quarter pieces cut from a 37 mm diameter wound dressing or 1.5 cm×1.5 cm wound dressing pieces cut from a larger wound dressing.

Control materials of Gelfoam™+thrombin or Surgicel™ were prepared from 1.5 cm×1.5 cm pieces. Gelfoam™ size 100, absorbable gelatin wound dressing, was supplied by Pharmacia. Oxidized cellulose, Surgicel™, was supplied by Ethicon. Topical thrombin (bovine origin) 10,000 U.S. units was supplied by Jones Pharma. The Gelfoam™+thrombin was prepared before use by soaking of 1.5 cm×1.5 cm×0.8 cm wound dressings in the thrombin for 30 minutes.

A midline ventral laporatomy was performed. The top half of the spleen was exteriorized (apposing the surgical wound with towel clamps). The surface was kept moist by the application of sterile saline solution from a wet lap pad.

For anticoagulation, the right femoral artery was surgically isolated and cannulated with a 6F sheath, allowing for collecting blood samples. The activated clotting time (ACT) was measured before administration of 5000 units of heparin intravenously, 10 minutes after administration of heparin and every 20 minutes thereafter. If the ACT level was less than 200 seconds, 2000 units of heparin were given and the ACT was remeasured after 10 minutes. This was repeated until the ACT>200 seconds to ensure that the animal was anticoagulated.

The area of splenic testing was demarcated and kept moist by using the towel clamps and wet pads and only exposing the most immediate untested surface.

A single injury was made prior to the application of a test patch, as follows:
  (i) In the laceration model, the injury (8 mm long×4 mm deep) was made using a #11 surgical blade positioned in a right-angled forceps so that 4 mm of blade was protruding.
  (ii) In the capsular stripping model, the injury (5 mm×5 mm×4 mm deep) was made using the clamped #11 blade and a pair of surgical scissors.

After making the injury, bleeding was allowed for 30 seconds. The surface blood was removed with gauze, following which a test patch was applied digitally to the injury using a constant uniform pressure for 30 seconds. The digital pressure was then removed and the patch was observed for two minutes. At this stage, the trial number was recorded. If observable rebleeding occured, the time to rebleed was recorded and the next trial (30 second bleed, clean away blood with gauze, 30 seconds digital pressure followed by up to 2 minutes observation) commenced. The trial for a test patch was complete when no rebleeding occurred in the 2 minute observation period or if 6 trial rebleeds were observed. If the wound continued to rebleed for 6 trial periods, then the failed patch was removed and a Gelfoam+thrombin patch applied. A new injury was made and another patch tested.

In the case of the carotid laceration model, chitosan patches (37 mm×25 mm) were cut from the 37 mm diameter compressed wound dressing or larger wound dressings. For facility in application, some of the wound dressings had a top layer of 3M 9781 foam medical tape attached to the chitosan with 3M 9942 skin adhesive. Gelfoam™+thrombin was used as a control.

A vertical incision was made exposing a 10 cm length of carotid artery. The fascia was retracted and the surrounding soft tissue was dissected until the artery was supported on a flat base of tissue. Tie-off sutures were placed proximal and distal to the exposed artery. These were clamped and a 1.5 cm incision was made longitudinally in the artery.

For anticoagulation, the right femoral artery was surgically isolated and cannulated with a 6F sheath, allowing for collecting blood samples. The activated clotting time (ACT) was measured before administration of 5000 units of heparin intravenously, 10 minutes after administration of heparin and every 20 minutes thereafter. If the ACT level was less than 200 seconds, 2000 units of heparin were given and the ACT was remeasured after 10 minutes. This was repeated until the ACT>200 seconds to ensure that the animal was anticoagulated.

After making the incision, the artery was allowed to bleed for 2 seconds and then was compressed for 1 minute. The compression was removed and the ties were re-clamped. The area was flushed with saline. The ties were unclamped 2 seconds before application of a patch. Pressure was applied uniformly over the patch for 3 minutes. If bleeding was observed within 30 minutes after application of pressure, then another 3 minutes of pressure was re-applied. If the patch was not adhering then it was replaced with a new patch. Each re-application of pressure, or replacement of a patch of the same type were treated as trial periods for that patch type. A trial for a particular wound dressing was considered complete if no bleeding was observed from around, or through the patch in a 30 minute period. A material was rated on the number of trials it took to achieve 30 minutes of hemostasis (no observable bleeding from the wound).

In the case of swine aorta perforation, sample patches of compressed chitosan wound dressing cut to 2.5 cm diameter pieces or controls of 4"×4" surgical gauze were used.

Either or both the abdominal and the thoracic aortas were exposed by midline ventral laporatomies in the former and sternotomies in the latter. The fascia and sternum were clamped and ties were placed proximal and distal to the sites of incision. While the tie-off clamps were applied, a #11 scalpel blade was used to make a 3 mm incision through the wall of the aorta and a 4 mm diameter Medtronic™ vascular punch was inserted through the incision to make a 4 mm diameter hole in the aorta. The punch was removed and the tie-off clamps released with digital pressure applied to the hole.

The patch was held between thumb and forefinger with the middle finger applying pressure to the hole in the aorta. The pressure from this middle finger was released for 1 second before application of the wound dressing to the bleeding field. The wound dressing was held in place by firm pressure applied through the forefinger to the patch over the aortic hole. The pooled blood that escaped the wound during application of the patch was suctioned away. After 3 minutes of digital pressure, the finger was removed and the patch observed for any sign of continued bleeding and poor adherence.

If continued bleeding or re-bleeding was observed in the first 30 minutes after application of the patch, then a further 3 minutes of pressure was applied. If hemostasis was still not complete, then another patch of the same wound dressing was prepared, the old patch removed and a new trial commenced. A trial was considered complete if no bleeding was observed from around or through the patch in a 30-minute period. A material was rated on the number of trials it took to achieve 30 minutes of hemostasis (no observable bleeding from the wound). Control samples of gauze were applied in the same manner as the chitosan wound dressing during a trial.

All animals were euthanized while under anesthesia with an injection of barbiturates (Euthasol, 1 ml/10 lb) via an auricular vein. Animals were euthanized at the end of the experimental procedure or prior to the end if the animal experienced any untoward effects.

Tests were ranked from 0.0 to 6.0 according to the number of trials necessary before hemorrhage control was achieved and the time to rebleed (only in the case of the spleen trials). A test in which only one trial was necessary and there was no rebleed was ranked as 0.0. A test which required a second trial and the time to rebleed of the first was 90 seconds was ranked:

$$1.0 + \frac{120-90}{120} = 1.25$$

(in the case of a spleen) or 1.0 in the other models.

A test which needed four trials to achieve hemostasis and where the time to splenic rebleed in the third trial was 30 seconds was ranked:

$$3.0 + \frac{120-30}{120} = 3.75$$

(in the case of a spleen) or 3.0 in the other models.

A sample which failed completely by rapid dissolution, lack of adherence or uncontrolled bleeding was ranked 6.0+.

In summary, the worse the hemostasis, the higher the ranking as defined by the following:

$$R = \Gamma + \Lambda$$

Where $\Gamma$ = number of trials to stop bleeding− 1

$$\Lambda = \frac{A - \text{time to rebleed(s) in previous trial}}{A}$$

$A$ = time of trial(s)

The results of the spleen studies are summarized in Tables 2, 3 and 4.

Table 2 shows the behavior of chitosan test samples that were non-optimized with respect to composition and structure. These non-optimized materials ranged from, worse to the Surgicel™ negative control (Table 4), to comparable and to only partially better. The presence of phosphate buffer solution produced a poorly adherent, slowly hemostatic patch which was only slightly more effective than Surgicel™. The chitosan film was moderately adherent, providing a reasonable seal to bleeding, however it was only very slowly hemostatic as evidenced by the slow welling of blood beneath its transparent surface. The earlier trials generally showed signs of a low density foam in the top surface of the molded wound dressing. It was found that this low density foam was susceptible to dissolution and collapse if the top surface of the wound dressing was applied to a bleeding field. It was subsequently discovered that this foam effect could be avoided by degassing of solutions before freezing. Low molecular weight chitosan wound dressings (relative 1% solution viscosity<50 cps) were found to be very susceptible to dissolution in a bleeding field making them unsuitable for the patch application. The glutamate counter anion produced softer wound dressings but at the cost of producing wound dressings that were readily dissolved in a severely bleeding field. Low density wound dressings (those less than 0.05 g/cm$^3$) with acetate counterions were also found to be readily compromised by dissolution and collapse.

Table 3 shows the result rankings of the optimized chitosan wound dressings of preferred composition and structure. These wound dressings were composed of chitosan with higher molecular weights (relative 1% solution viscosity greater than 100 cps) and had wound dressing densities close to 0.12 g/cm$^3$. In the moderately bleeding spleen tests, the results for the optimized wound dressings were found, using a Wilcoxon Rank Sum W Test, to be indistinguishable from the positive control of Gelfoam™+thrombin (Z=−0.527, p=0.598). Using the same statistical method, the wound dressings were shown to be significantly different from the poorly performed Surgicel™ control (Z=−3.96, p=0.0001).

Figure 6:
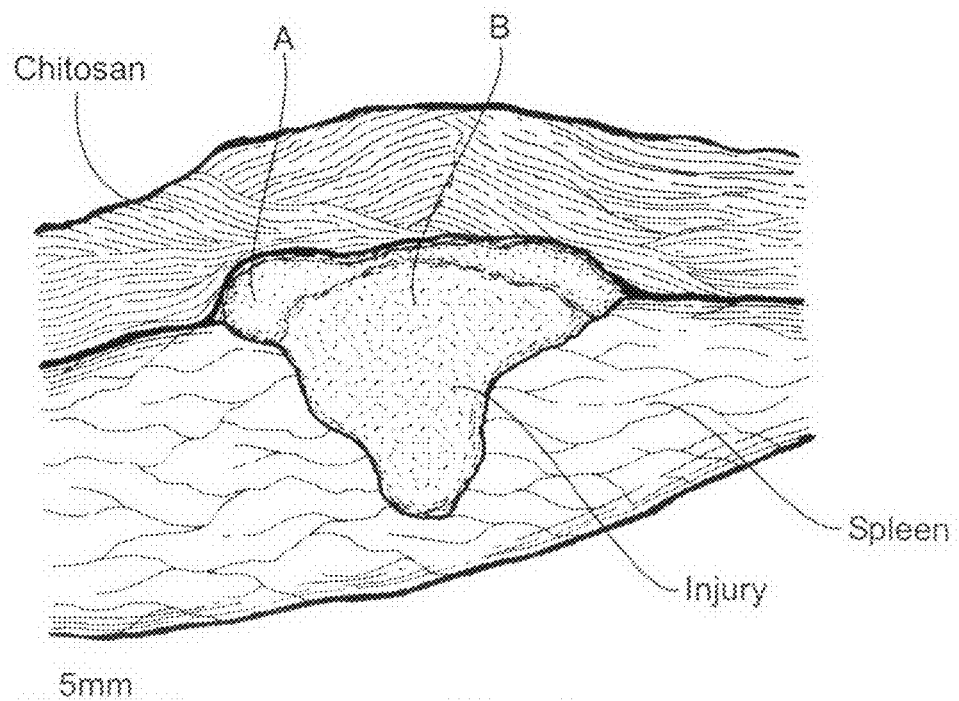
FIG. 6. Histological stained section through chitosan/spleen injury site and adjacent splenic surface. Agglutinated clot response (A) with a mixture of fibrin/platelet rich blood clot (B) between patch and spleen. Very good adhesion between is spleen and chitosan FIG. 7. Photograph of thoracic aorta injury sealed with chitosan patch FIG. 8. Fixed thoracic aorta demonstrating perforation injury FIG. 9. Stained histological section through thoracic aorta injury FIG. 10. Photograph of in vitro burst pressure failure in a strongly adherent dressing FIG. 11. Histogram of water and blood adsorption results for gamma irradiated and un-irradiated (unsterilized) samples.

FIG. 6 demonstrates (via a H&E stained histological section) the close adherence of the optimized chitosan wound dressings patches to the spleen surface as well as the agglutination of erythrocytes at the immediate vicinity of the injury.

The rankings for the carotid injury model are summarized in Table 5. In this model, the optimized chitosan patch performed very well in trials 3, 5 and 6. The improvement in performance over the first trials 1 and 2 was due to the application of the support backing (3M 9781 foam bandage) to the immediate top surface of the wound dressing. This backing enabled more uniform pressure to be applied over the wound dressing and allowed for the person applying the dressing to remove their fingers easily from the patch surface without them sticking and inducing patch detachment from the wound. The carotid model was used to investigate more severe arterial bleeding conditions than were possible in the spleen injury model. Gelfoam™+thrombin was investigated as a possible positive control but was found to dissolve in a highly bleeding field.

Figure 7:
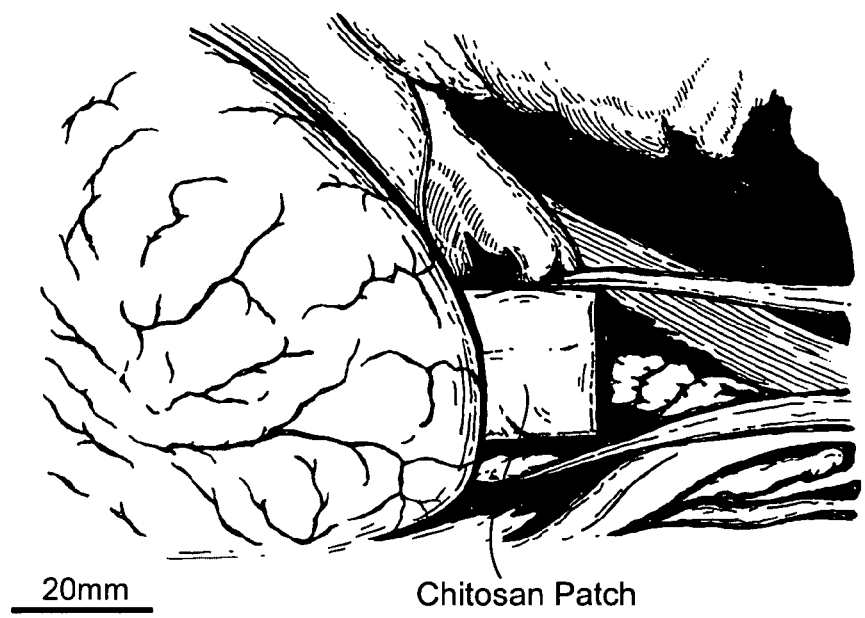
Figure 8:
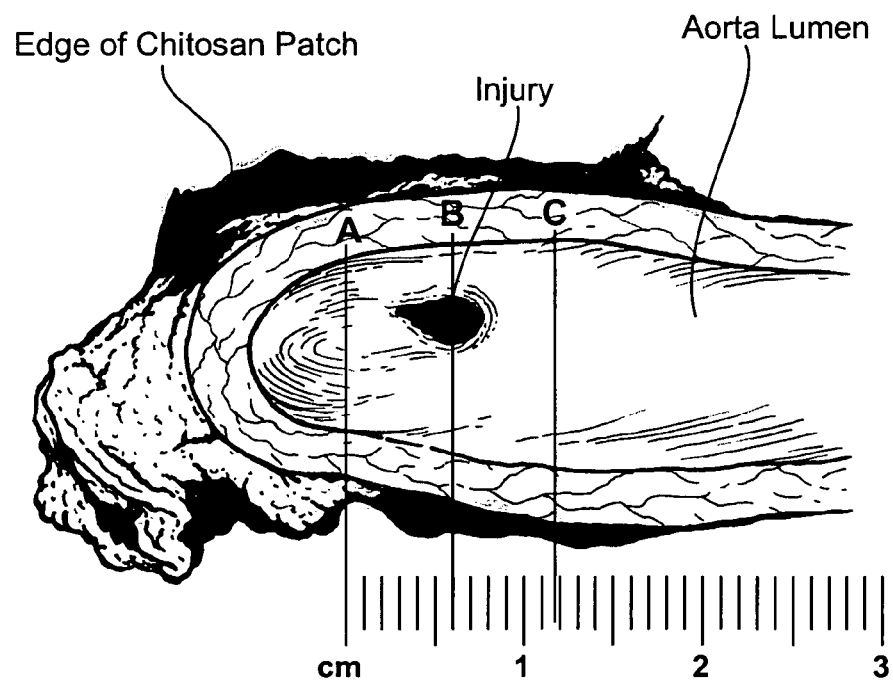
Figure 9:
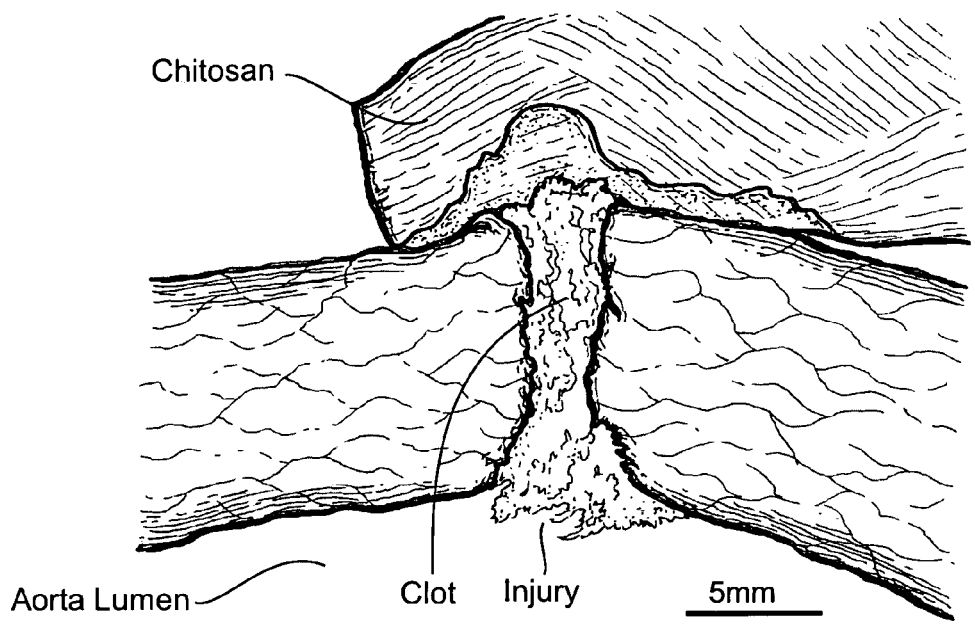

Table 6 summarizes the results of the aortic injury model. Gauze bandage (4"×4") was used as a control bandage. It was found that the control was unable to stop severe bleeding in all trial periods whereas the optimized chitosan aortic patches were able quickly to stop and subsequently clot the very high level of bleeding observed in this wound after only 1 or 2 applications of the patch. The exact significance (two-tailed p=0.002) was determined for the probability that there was no difference between rankings of sample and control. On average the blood loss after patch application was minimal (<50 ml) if the wound was stanched on the first attempt. If a second attempt was required blood loss after patch application was greater than 100 ml but less than 300 ml. On average less than 150 ml of blood was lost after patch application in the case of the chitosan wound dressing while, in the case of the 3 gauze control studies, more than 1 liter of blood was lost for each animal. In the case of the chitosan wound dressing study, survival was 100%, while in the case of the gauze study, none (0%) of the animals survived. The chitosan patches demonstrated continued hemostatic efficacy over the trial period of 30 minutes and until the animals were sacrificed which was generally 1 to 2 hours later. FIG. 7 demonstrates a typical chitosan patch sealing a severe thoracic wound. The lumen side (showing the injury) of the resected aorta sealed by the patch in FIG. 7 is shown in FIG. 8. FIG. 9 shows a photomicrograph of a stained histological section taken through the injury of FIGS. 7 & 8. Evidence of strong clotting at the injury site was found on removal and inspection of aortas on animal sacrifice (FIG. 9) and, in the case of trial number 16, where after dislodging a patch in a live animal (after more than 30 minutes of application) there was no subsequent re-bleeding.

TABLE 2

| Animal | Sample Type | Sample Source | Sample Name | Sample Batch | Sample Form | Model Anticoagulat. | Model Injury | Result Rank | Result Comments |
|---|---|---|---|---|---|---|---|---|---|
| 1346 | Chitosan | Carbomer | 9012-75-4 | VA-UY992 | PBS treat | No | Laceration | 4.0 | Poor adhesion + slow hemostasis |
| 1346 | Chitosan | Carbomer | 9012-75-4 | VA-UY992 | Film type | No | Laceration | 2.7 | Adhesive + slow hemostatic |
| 1345 | Chitosan | Carbomer | 9012-75-4 | VA-UY992 | PBS treat | No | Laceration | 5.6 | Poor Adhesion + poor hemostasis |
| 1338 | Chitosan | Primex | Chitoclear | TM 752 | Dense type | Yes | Laceration | 3.1 | Slow bleed through low density defect in wound dressing |
| 1338 | Chitosan | Pronova | G113 | 005-370-01 | Dense type | Yes | Capsular | 6.0+ | Low Mw Chitosan dissolved |
| 1338 | Chitosan | Pronova | G113 | 005-370-01 | Dense type | Yes | Capsular | 6.0+ | Low Mw Chitosan dissolved |
| 1338 | Chitosan | Pronova | G213 | 511-583-01 | Dense type | Yes | Capsular | 6.0 | Softer Chitosan Collapsed |
| 1338 | Chitosan | Pronova | G213 | 511-583-01 | Dense type | Yes | Capsular | 6.0 | Softer Chitosan Collapsed |
| 1441 | Chitosan | Primex | Chitoclear | BN 381 | LD type, FF type | Yes | Capsular | 1.8 | Good adhesion + initial small bleed through |
| 1441 | Chitosan | Primex | Chitoclear | BN 381 | Dense type, FF type | Yes | Capsular | 1.8 | Good adhesion + initial small bleed |

Dense type = Dense wound dressing (ca. 0.12 g/cm$^3$)
PBS treat = A wound dressing neutralized by soaking in phosphate buffer saline solution
LD type = Low density wound dressing (ca. 0.03 g/cm$^3$)
FF type = A fast frozen wound dressing
Film type = a solvent cast film (500 microns)

TABLE 3

| Animal | Sample Type | Sample Source | Sample Name | Sample Batch | Sample Form | Model Anticoagulat. | Model Organ | Model Injury | Result Rank | Result Comments |
|---|---|---|---|---|---|---|---|---|---|---|
| 1346 | Chitosan | Carbomer | 9012-75-4 | VA-UY992 | Dense type | No | Spleen | Laceration | 0.0 | Good adhesion + rapid hemostasis |
| 1404 | Chitosan | Primex | Chitoclear | BN 381 | Dense type | No | Spleen | Laceration | 0.0 | Good adhesion + rapid hemostasis |
| 1404 | Chitosan | Carbomer | 9012-75-4 | VA-UY992 | Dense type | No | Spleen | Laceration | 0.0 | Good adhesion + rapid hemostasis |
| 1404 | Chitosan | Primex | Chitoclear | BN 381 | Dense type | Yes | Spleen | Capsular | 0.0 | Good adhesion + rapid hemostasis |
| 1338 | Chitosan | Primex | Chitoclear | TM 752 | Dense type | Yes | Spleen | Laceration | 0.0 | Good adhesion + rapid hemostasis |
| 1338 | Chitosan | Primex | Chitoclear | TM 752 | Dense type | Yes | Spleen | Laceration | 0.0 | Good adhesion + rapid hemostasis |
| 1338 | Chitosan | Primex | Chitoclear | TM 752 | Dense type | Yes | Spleen | Capsular | 0.0 | Good adhesion + rapid hemostasis |
| 1338 | Chitosan | Primex | Chitoclear | TM 752 | Dense type | Yes | Spleen | Capsular | 0.0 | Good adhesion + rapid hemostasis |
| 1338 | Chitosan | Primex | Chitoclear | TM 752 | Dense type | Yes | Spleen | Capsular | 0.0 | Good adhesion + rapid hemostasis |
| 1338 | Chitosan | Primex | Chitoclear | TM 752 | Dense type | Yes | Spleen | Capsular | 0.0 | Good adhesion + rapid hemostasis |
| 1344 | Chitosan | Pronova | CL213 | 607-783-02 | Dense type | Yes | Spleen | Capsular | 0.0 | Good adhesion + rapid hemostasis |
| 1344 | Chitosan | Primex | Chitoclear | TM 752 | Dense type | Yes | Spleen | Capsular | 0.0 | Good adhesion + rapid hemostasis |
| 1441 | Chitosan | Primex | Chitoclear | TM 752 | Dense type | Yes | Spleen | Capsular | 0.0 | Good adhesion + rapid hemostasis |
| 1441 | Chitosan | Primex | Chitoclear | TM 752 | Dense type | Yes | Spleen | Capsular | 0.0 | Good adhesion + rapid hemostasis |
| 1441 | Chitosan | Primex | Chitoclear | TM 752 | Dense type | Yes | Spleen | Capsular | 0.0 | Good adhesion + rapid hemostasis |
| 1441 | Chitosan | Primex | Chitoclear | TM 752 | Dense type | Yes | Spleen | Capsular | 1.3 | Good adhesion + initial slight local bleeding |
| 1478 | Chitosan | Primex | Chitoclear | TM 751 | Dense type | Yes | Spleen | Capsular | 0.0 | Good adhesion + rapid hemostasis |
| 1478 | Chitosan | Primex | Chitoclear | TM 751 | Dense type | Yes | Spleen | Capsular | 0.0 | |
| | | | | | | | | Mean | 0.1 ±0.31 | |

Dense type = Dense wound dressing (ca. 0.12 g/cm$^3$)

TABLE 4

| Animal | Sample Type | Sample Source | Sample Name | Sample Form | Model Anticoagulat. | Model Injury | Result Rank | Result Comments |
|---|---|---|---|---|---|---|---|---|
| 1338 | Control | Pharmacia | Gelfoam + thr | Sponge | Yes | Capsular | 0.0 | Satisfactory adhesion + rapid hemostasis |
| 1344 | Control | Pharmacia | Gelfoam + thr | Sponge | Yes | Capsular | 0.0 | Satisfactory adhesion + rapid hemostasis |
| 1344 | Control | Pharmacia | Gelfoam + thr | Sponge | Yes | Capsular | 0.0 | Satisfactory adhesion + rapid hemostasis |
| 1441 | Control | Pharmacia | Gelfoam + thr | Sponge | Yes | Capsular | 0.0 | Satisfactory adhesion + rapid hemostasis |
| 1441 | Control | Pharmacia | Gelfoam + thr | Sponge | Yes | Capsular | 0.0 | Satisfactory adhesion + rapid hemostasis |
| | | | | | | Mean | 0.0 ±0.0 | |
| 1338 | Control | Ethicon | Surgicel | Gauze | Yes | Laceration | 5.9 | Very slow hemostasis |
| 1441 | Control | Ethicon | Surgicel | Gauze | Yes | Capsular | 3.9 | Very slow hemostasis and poor adhesion |
| 1441 | Control | Ethicon | Surgicel | Gauze | Yes | Capsular | 5.9 | Very slow hemostasis and poor adhesion |
| | | | | | | Mean | 5.2 ±1.15 | |

TABLE 5

| Trial Number | Animal | Sample Type | Sample Source | Sample Name | Sample Batch | Sample Form | Model Anticoagulat. | Model Injury | Result Rank | Result Comments |
|---|---|---|---|---|---|---|---|---|---|---|
| 1 | 1404 | Chitosan | Primex | Chitoclear | BN 381 | Dense type | Yes | Laceration | 3 | First trial injury. Profuse bleeding at site prior to application, first 3 applications slowed bleeding final application closed wound area not initially covered. |
| 2 | 1335 | Chitosan | Primex | Chitoclear | TM 752 | Dense type | Yes | Laceration | 4 | Non-backed sample. Problem with pressure application without damaging wound dressing in bleeding field. |
| 3 | 1335 | Chitosan | Pronova | CL213 | 607-783-02 | Dense type | Yes | Laceration | 0 | 3M backing enabled pressure application without damaging wound dressing. |
| 5 | 1442 | Chitosan | Primex | Chitoclear | TM 752 | Dense type | Yes | Laceration | 0 | 3M backing + Good adhesion & rapid hemostasis. |
| 6 | 1442 | Chitosan | Primex | Chitoclear | TM 752 | Dense type | Yes | Laceration | 1 | 3M backing + Good adhesion & rapid hemostasis. |
| 4 | 1441 | Control | Pharmacia | Gelfoam + th | | Sponge | Yes | Laceration | 6+ | Unable to stop bleeding as Gelfoam dissolved in bleeding field and was non-adherent |

Dense type = dense sponge wound dressing (ca. 0.12 g/cm$^3$)

TABLE 6

| Trial Number | Animal | Sample Type | Sample source | Sample Name | Sample Batch | Sample Form | Model Anticoagulat. | Aorta | Model Injury | Result Rank | Result Comments |
|---|---|---|---|---|---|---|---|---|---|---|---|
| 1 | 1465 | Chitosan | Primex | Chitoclear | TM 752 | Dense type | No | Abdom. | 4 mm perfor. | 0 | No backing. Sealed for 4 mins then bled through. |
| 2 | 1465 | Chitosan | Primex | Chitoclear | TM 752 | Dense type | No | Abdom. | 4 mm perfor. | 0 | 3M backed. Sandwich around Aorta. Hemostatic & adherent after 30 mins. |
| 3 | 1470 | Chitosan | Primex | Chitoclear | TM 752 | Dense type | No | Thor. | 4 mm perfor. | 0 | 3M backed. Remaining hemostatic & adherent after 30 mins. |
| 4 | 1468 | Chitosan | Primex | Chitoclear | TM 752 | Dense type | No | Thor. | 4 mm perfor. | 0 | 3M backed. Remaining hemostatic & adherent after 30 mins. |
| 5 | 1462 | Chitosan | Primex | Chitoclear | TM 752 | Dense type | No | Thor. | 4 mm perfor. | 1 | 3M backed. First patch Temporarily adherent. Second Patch remaining hemostatic & adherent after 30 mins. |
| 6 | 1460 | Chitosan | Primex | Chitoclear | TM 752 | Dense type | No | Thor. | 4 mm perfor. | 0 | 3M backed. Remaining hemostatic & adherent after 30 mins. |
| 7 | 1460 | Chitosan | Primex | Chitoclear | TM 752 | Dense type | No | Abdom. | 4 mm perfor. | 1 | 3M backed. First patch slipped off. Second Patch remaining hemostatic & adherent after 30 mins. |
| 8 | 1461 | Chitosan | Primex | Chitoclear | TM 752 | Dense type | No | Thor. | 4 mm perfor. | 0 | 3M backed. Remaining hemostatic & adherent after 30 mins. |
| 9 | 1461 | Chitosan | Primex | Chitoclear | TM 752 | Dense type | No | Abdom. | 4 mm perfor. | 0 | 3M backed. Remaining hemostatic & adherent after 30 mins. |
| 10 | 1469 | Chitosan | Primex | Chitoclear | TM 752 | Dense type | No | Thor. | 4 mm perfor. | 3 | 3M backed. First 3 patches slipped off. Fourth patch remained hemostatic & adherent after 30 mins |
| 11 | 1469 | Chitosan | Primex | Chitoclear | TM 752 | Dense type | No | Abdom. | 4 mm perfor. | 0 | 3M backed. Sandwich necessary as aorta perforated above and bel Second patch remained adherent & hemostatic over trial |
| 12 | 1467 | Chitosan | Primex | Chitoclear | TM 751 | Dense type | No | Abdom. | 4 mm perfor. | 1 | 3M backed. First Patch removed after bleeding through side in first 5 mins. Second patch remained adherent & hemostatic over tr |
| 13 | 1467 | Chitosan | Primex | Chitoclear | TM 751 | Dense type | No | Abdom. | 4 mm perfor. | 1 | 3M backed. First Patch removed after collapsing in first 5 minutes Second patch remained adherent & hemostatic over trial |
| 14 | 1398 | Chitosan | Primex | Chitoclear | TM 751 | Dense type | No | Abdom. | 4 mm perfor. | 0 | 3M backed. Remaining hemostatic & adherent after 30 mins. |
| 15 | 1398 | Chitosan | Primex | Chitoclear | TM 751 | Dense type | No | Thor. | 4 mm perfor. | 1 | 3M backed. First patch slipped off. Second Patch remaining hemostatic & adherent after 30 mins. |
| 16 | 1399 | Chitosan | Primex | Chitoclear | TM 751 | Dense type | No | Abdom. | 4 mm perfor. | 0 | 3M backed. Remaining hemostatic & adherent after 30 mins. Knocked off while making second nearby injury after 40 minutes. Injury had completely clotted over. |
| 17 | 1399 | Chitosan | Primex | Chitoclear | TM 751 | Dense type | No | Abdom. | 4 mm perfor. | 2 | 3M backed. First 2 patches slipped off. Third patch remained hemostatic & adherent after 30 mins. |
| 18 | 1479 | Chitosan | Primex | Chitoclear | TM 751 | Dense type | No | Abdom. | 4 mm perfor. | 1 | 3M backed. First patch slipped off. Second Patch remaining hemostatic & adherent after 30 mins. |
| 19 | 1479 | Chitosan | Primex | Chitoclear | TM 751 | Dense type | No | Thor. | 4 mm perfor. | 2 | 3M backed. First 2 patches slipped off. Third patch remained hemostatic & adherent after 30 mins. |
| | | | | | | | | | Mean | 0.7 | |
| | | | | | | | | | | ±0.89 | |
| 20 | 1483 | Control | J&J | | | Gauze | No | Abdom. | 4 mm perfor. | 6+ | After 15 minutes animal became hypotensive and was euthanized |
| 21 | 1489 | Control | J&J | | | Gauze | No | Abdom. | 4 mm perfor. | 6+ | After 15 minutes animal became hypotensive and was euthanized |
| 22 | 1490 | Control | J&J | | | Gauze | No | Thor | 4 mm perfor. | 6+ | After 15 minutes animal became hypotensive and was euthanized |

Dense type = dense sponge wound dressing (ca. 0.12 g/cm$^3$)

Preferably, the hemorrhage control dressing described above includes a surface, which grips the wound area to substantially avoid slipping of the dressing during use. Typically, this non-slip surface of the dressing comprises a traction surface. The subject hemorrhage control dressing may benefit from having an effective non-slip surface, such as a traction surface. The subject hemorrhage control dressing can have a smooth and rough side. The rougher side would preferably be the tissue or bleeding surface side if that side also demonstrated better adhesive properties.

A traction surface may improve a dressing ability to control rapid arterial bleeding by providing increased stability of surface contact (better traction) on a well lubricated surface (such as those surfaces which present in the case of severe bleeding). Such a traction surface would help to channel blood, without adversely affecting adhesion kinetics while allowing for a more controlled and stable tissue contact during the critical period of dressing application. For example, the tissue side of the bandage could have a traction surface in the form of a tread design. This could prevent the dressing from undergoing traction loss in a direction away from the wound when undergoing application to the wound.

The non-slip surface of the hemorrhage control dressing could be produced with ridges that are non-connecting or blinded to one another. Thus, in turn, the channels formed between the ridges would be fully or partially blinded to one another and thus provide a controlled connection that would provide for a controlled blood flow back into or out of the wound area. The controlled blood flow in area of dressing application could be maintained by the ridges or specific types of responsive gates in the hemorrhage control dressing. Ridges on bottom of a mold for producing the hemorrhage control dressing may include depressions of the type which will permit a non-slip surface, for example, in the form of traction controls such as ridges or the like, in the subject dressings.

A hemorrhage control dressing could therefore be produced having at least one non-slip surface, such as a traction surface. Also, a method of producing such a dressing could be provided. Finally, a mold to a produce a hemorrhage control dressing, as described above, can be fabricated.

So as to treat severe hemorrhage in cases where adhesive base and top surfaces are advantageous, it is possible to design the support backing so that if necessary it could be readily peeled away when adhesion and clotting are required on both surfaces.

There are numerous hemorrhage control configurations of the dressing described above to address a wide range of possible types of hemorrhagic wound. It is envisioned there be will a need to be able to carry (in a battlefield situation) several bandages of differing configurations so that the injured persons can be treated by the first responder or even potentially by injured persons themselves. The dressing of the invention claim is robust and can tolerate a great deal of physical abuse and still remain an active hemorrhage control platform.

The dressing is ideal for treating focal vascular bleeding and small topical wounds. It is also well suited to packing into complex entry wounds where the bleeding site cannot be easily compressed.

Once hemorrhage control is achieved with the current invention, stabilizing an extremity wound, approximating wound edges and creating a durable dressing that will prevent contamination and allow evacuation of the injured for definitive repair are the main requirements for a civilian and a battlefield hemorrhage control dressing.

One envisioned configuration of the hemorrhage control dressing is a 10"×18" dressing with a flexible, elastic backing that can be tightly attached around an extremity and secured with a locking tab such as a permanent adhesive glue via a peel back surface to itself. Such a device configuration would approximate wound surfaces and add a hemorrhage control surface without compromising blood flow to the distal extremity. Such a dressing could be applied by a first responder or in some instances by the injured soldier and would be stable under ambulation or extremity movement during transport. It is envisioned that the bandage would be removed by cutting it apart with no adverse adhesion to the wound or skin.

The US Army Science and Technology Objective (STO) A, Hemorrhage Control, was established in 2000 to advance the need for hemorrhage control on the battlefield. The general strategic objective of the STO can be summarized as the development of products and methods that will reduce the number of deaths due to hemorrhage in battlefield casualties. The requirements for hemorrhage control products and methods were stated thus:

They must be practicable for use by one or more of the following: self (wounded combatant), buddy (fellow non-medical soldier who aids the wounded soldier), combat lifesaver, combat medic, physician assistant, and battalion surgeon. They must be practicable for use in far forward field conditions including rugged terrain, limited visibility, and environmental extremes. Products and methods must not require external electrical sources. All devices must be man-portable and durable. It is expected that products and methods that are useable far forward will also be used at higher echelons of care. A specific strategic objective of the STO is the development of new or improved hemostatic agents for use on compressible hemorrhage under far forward field conditions. A single product for use on compressible and non-compressible sites is desired.

As part of STO, a study of hepatic hemorrhage control in a swine liver model was conducted at the US-Army Institute of Surgical Research (ISR) at Fort Sam Houston, San Antonio, Tex. using the hemorrhage control bandage of this invention. The study was conducted to determine the effect of the chitosan hemorrhage control bandage on blood loss and survival in a standardized model of severe venous hemorrhage and hepatic injury in swine. This model has been used to study numerous other hemostatic bandages at US-Army ISR.

Cross-bred commercial swine were used in this study. Animals were maintained in a facility accredited by the Association for the Assessment and Accreditation of Laboratory Animal Care, International. This study was approved by the Institutional Animal Care and Use Committee of the US Army Institute of Surgical Research, Fort Sam Houston, Tex. Animals received humane care in accordance with the Guide for the Care and Use of Laboratory Animals (National Institutes of Health publication 86-23, revised 1996).

Animals were assigned randomly to receive either the Chitosan bandages or Gauze sponges (see Table 7). Surgical preparation consisted of the following: Animals were fasted 36-48 hours prior to the surgical procedure, with water allowed ad libidum. After premedication with glycopyrrolate and a combination of tiletamine HCl and zolazepam HCl (Telazol®, Fort Dodge Laboratories, Fort Dodge, Iowa), anesthesia was induced by mask using 5% isoflurane. The swine were intubated, placed on a ventilator, and maintained with isoflurane. Carotid arterial and jugular venous catheters were placed surgically. Laparotomy was performed and splenectomy and urinary bladder catheter placement were completed. A rectal temperature between 37.0° and 39.0° C., and 15 minutes of stable mean arterial pressures (MAP) were required prior to further experimental procedures. Blood pressure and heart rate were recorded at 10-second intervals throughout the study period using a continuous data collection system (Micro-Med®, Louisville, Ky.). Baseline arterial blood samples were collected from each animal to confirm that each animal exhibited normal platelet count, prothrombin time, activated partial thromboplastin time, and plasma fibrinogen concentration.

Liver injuries were induced as previously reported. The method included the following. The liver was retracted by manually elevating the left and right medial lobes to allow adequate exposure. Next, a specially designed clamp with two 4.5 cm sharpened tines configured in the form of an 'X' was positioned with the center approximately 2-3 cm dorsal to the intersection of the left and right medial lobes, on the diaphragmatic surface of the liver. The base plate of the instrument was positioned beneath the quadrate lobe, on the visceral surface. The injury was induced by clamping the tines of the instrument through the parenchyma and underlying vessels of the two medial lobes so that the tines were seated in corresponding grooves in the base plate of the instrument. After the first penetration of the liver, the instrument was opened and the tines were withdrawn and repositioned to the animals left such that the second application would overlap the first by 50 percent. Following this repositioning, the liver was penetrated a second time. Documentation of the liver injury was achieved by excision and inspection of the liver at the conclusion of the experimental period. The injuries appeared as large stellate wounds with a small island of tissue in the center, and measured approximately 10×8×4 cm. The injuries were through and through, with one or more of the left medial lobar vein, right medial lobar vein, and portal hepatic vein lacerated.

Thirty seconds after injury, resuscitation was initiated with warm (38° C.) lactated Ringer's solution in all animals. The goal of resuscitation was return to baseline MAP. Fluid was administered at 260 ml/min. This resuscitation regimen was continued until the goal was reached and reinitiated if MAP decreased, throughout the 60 minute study period. Simultaneously with initiation of resuscitation (30 seconds post-injury), treatments were applied as follows. One dressing was applied to the surface of the quadrate lobe to cover the penetrating injury and two other dressings were stuffed into the injury from the diaphragmatic aspect. Compression was applied for 60 seconds in the dorso-ventral direction. After 60 seconds, the injury was inspected to determine whether hemostasis was achieved. Next, the applicator's hands were repositioned and pressure was applied for 60 seconds in the latero-medial direction, and the observation for hemostasis was performed. This sequence was repeated for a total of four 60 second compressions. If hemostasis was complete after any compression, no further compressions were performed. Hemostasis was defined as the absence of visually detectable bleeding from the injury site.

Following completion of treatment application, the abdomen was closed and the animal was monitored for 60 minutes after injury or until death, whichever came first. Death prior to 60 minutes was defined as a heart rate of 0. At 60 minutes, surviving animals were euthanized by an overdose of pentobarbital.

Immediately after induction of the injury, blood was continuously suctioned from the peritoneal cavity until the start of treatment application. The volume was determined and designated as pre-treatment blood loss. At the end of the study period, each abdomen was opened and the liquid and clotted intra-peritoneal blood were suctioned and measured. This was designated as post-treatment blood loss. Additionally, total resuscitation fluid use was recorded. Preinjury animal blood volume was estimated using the equation: estimated blood volume (ml)=161.4751(body weight$^{-0.2197}$)(body weight), as we have previously reported (Pusateri, 2001).

Body weight, estimated blood volume, number of vessels lacerated, baseline MAP, survival time, preinjury MAP, pretreatment blood loss, and bandage adherence scores were analyzed by analysis of variance using the GLM procedure of SAS. Data are reported as least squares mean±standard error of least squares mean. Data were examined for heterogeneity of variance and non-normality. These conditions were detected for post-treatment blood loss and fluid use data. Therefore, blood loss and fluid use data were log transformed prior to analysis. The transformed data were analyzed by analysis of variance. These data are expressed as back transformed means and 95% confidence interval (95% CI). Distribution of females and males, hemostasis, and survival data were analyzed by Fishers Exact Test using the FREQ procedure of SAS. Data are reported as proportions or percentages. Two sided tests were used for all comparisons.

There were no differences among treatment groups in animal body weight, estimated blood volume, distribution of animal sexes, baseline MAP, preinjury MAP, number of major vessels lacerated within the liver injury, or pretreatment blood loss (See Tables 8 and 9).

Post-treatment blood loss was reduced in the Chitosan group, compared to the Gauze wound dressing control (p=0.01). No significant difference in fluid use was observed. Survival percentage was increased in the Chitosan group (p=0.04). Hemostasis occurred more frequently in the Chitosan group at 3 and 4 minutes post-injury (p=0.03). Survival times could not be statistically compared because of the high level of survival in the Chitosan group (See Table 10).

TABLE 7

| Test Material | Lot Number And Related Information |
|---|---|
| Gauze Dressing (Negative Control) | Johnson and Johnson NU Gauze Sponge General Use 10.2 cm × 10.2 cm. Rayon/Polyester Formed Fabric. Lot Number 1999-05 1399T5205B2. |
| Chitosan Wound dressing | Oregon Medical Laser Center, Chitosan Wound dressing, 10.2 cm × 10.2 cm. Lot Number 052101. Batch Number E1041. 26 May 2001 (1% AA, Primex Lot # 751). |

TABLE 8

| Variable | Gauze Sponge Control Group | Chitosan Group | P value of difference |
|---|---|---|---|
| n | 7 | 8 | N/A |
| Body Weight (kg) | 39.1 ± 1.2 | 38.7 ± 1.1 | 0.82 |
| Estimated Blood Volume (ml) | 2819 ± 66 | 2800 ± 64 | 0.83 |
| Female/Male (n/n) | 5/2 | 6/2 | 0.88 |
| Baseline MAP (mm Hg) | 71.3 ± 3.6 | 68.8 ± 3.3 | 0.50 |
| Preinjury MAP (mm Hg) | 69.1 ± 4.8 | 69.3 ± 4.4 | 0.98 |
| Hematocrit (%) | 32.2 ± 1.1 | 32.6 ± 1.0 | 0.79 |
| Hemoglobin (g/dL) | 11.2 ± 0.4 | 11.3 ± 0.3 | 0.80 |
| Platelets (1000/ul) | 567 ± 28 | 502 ± 25 | 0.11 |
| PT (sec) | 10.7 ± 0.2 | 10.6 ± 0.2 | 0.70 |
| aPTT (sec) | 15.7 ± 0.9 | 16.5 ± 0.9 | 0.56 |
| Fibrinogen (g/dL) | 159 ± 0.9 | 180 ± 8 | 0.10 |

TABLE 9

| Variable | Gauze Sponge Control Group | Chitosan Group | P value of difference |
|---|---|---|---|
| Number of Vessels Lacerated | 1.86 ± 0.29 | 1.88 ± 0.27 | 0.96 |
| Pretreatment Blood Loss (ml) | 296.1 ± 55.4 | 291.1 ± 55.4 | 0.95 |
| Pretreatment Blood Loss (ml/kg body weight) | 10.6 ± 2.0 | 10.3 ± 2.0 | 0.94 |

TABLE 10

| Variable | Gauze Sponge Control Group | Chitosan Group | P value of difference |
|---|---|---|---|
| Post-treatment Blood Loss (ml) | 2879 (788-10,513; 95% CI) | 264 (82-852; 95% CI) | <0.01 |
| Post-treatment Blood Loss (ml/kg body weight) | 102.4 (28.2-371.8) | 9.4 (2.9-30.3; 95% CI) | <0.01 |
| Fluid Use (ml) | 6614 (2,519-17,363; 95% CI) | 1793 (749-4,291; 95% CI) | 0.03 |
| Survival (%) | 28.6 | 87.5 | 0.04 |
| Survival Time (min; nonsurvivors only) | 38.4 ± 5.8 (n = 5) | 10.0 (n = 1) | N/A |
| Hemostasis at 1 Minute (%) | 0 | 50 | 0.08 |
| Hemostasis at 2 Minutes (%) | 0 | 50 | 0.08 |
| Hemostasis at 3 Minutes (%) | 0 | 62 | 0.03 |
| Hemostasis at 4 Minutes (%) | 0 | 62 | 0.03 |

This US-Army ISR study (Pusateri et al 2002) demonstrates, in an independent study, the significantly improved performance of the chitosan wound dressing over standard 4"×4" gauze. The US-Army ISR has only been able to demonstrate significantly improved performance over 4"×4" gauze in the stanching of severe blood flow in the case of the dressing of this invention claim and in the case of a dry Fibrin Thrombin wound dressing being developed by the Red Cross. The Red Cross Bandage is costly, as well as being delicate and prone to breakage.

High molecular weight 4"×4" chitosan hemorrhage control dressings with 3M 9781 porous foam backing have been prepared from an Icelandic shrimp source (Genis Lot#SO1115-1). These were prepared with 2% acetic acid and 2% chitosan solution using a commercial freeze drying company to prepare a large sterile lot of chitosan bandages (Lot#OMLC_2SM114). The bandages were irradiated at 15 kGy under nitrogen. They were subsequently tested for uniaxial tensile strength, burst strength, blood adsorption, water adsorption as well as for sterility. Swine aorta perforations were carried out on non-gamma irradiated samples in abdominal and thoracic injuries. Seven patches were used. On average blood loss after patch application was <50 ml. All patches were adherent, wound sealing and hemostatic on their first application (7×0 rankings). All animals survived.

Both gamma-irradiated and un-irradiated bandages (Lot#OMLC_2SM114) were tested with an in vitro burst pressure test developed at Oregon Medical Laser Center in Portland Oreg. To perform a burst test, a 25 mm diameter circular test piece of the bandage is immersed in citrated whole blood for 10 seconds. The test piece is then placed centrally over, and firmly held with digital pressure, on a 4 mm diameter perforation in the side of a 50 mm diameter PVC pipe for 3 minutes. After this initial attachment, fluid pressure inside the pipe is ramped at $4.5 \pm 0.5$ kPa.s$^{-1}$, with pressure and time recorded at 0.1 second intervals. Burst pressure is recorded as the maximum pressure recorded prior to failure. An adhesive failure ranking is assigned to assess the relative adhesiveness of the bandage to the test site. The ranking system is separated into 3 distinct modes of failure. A ranking of 1 is given to a test piece which is readily separated from the PVC surface with no chitosan remaining adhered. A ranking of 2 is assigned when the test piece is less readily detached and some of the chitosan remains attached to the test site. A ranking 3 is assigned when the test piece can only be removed by cohesive separation of the bulk wound dressing from the base structure which remains firmly fixed to the PVC surface.

Figure 10:
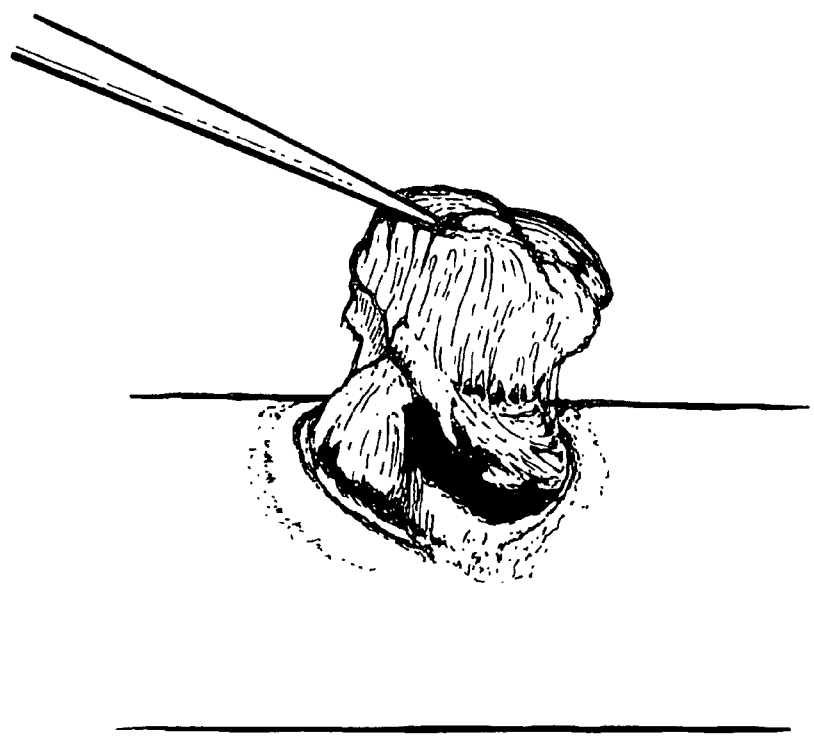

The average burst pressure of gamma irradiated and un-irradiated chitosan bandages (Mean±SD, n=6) on a PVC substrate using blood as wetting medium was 122±1.9 kPa and 86±20 kPa, respectively. The results were analyzed statistically using a T-test (p=0.007). The average adhesive failure rankigs of gamma irradiated and un-irradiated chitosan alpha bandages (Mean±SD, n=6) on a PVC substrate using blood as wetting medium were both 3±0. FIG. 10 shows an image of a high ranking failure where cohesive failure has occurred within the chitosan structure.

The blood and water adsorption properties of the dressings (Lot# OMLC_2SM114) were determined by immersing small test pieces (ca. 0.02 g) in blood or water for 3.0 seconds. Difference in mass before and after immersion was recorded.

Figure 11:
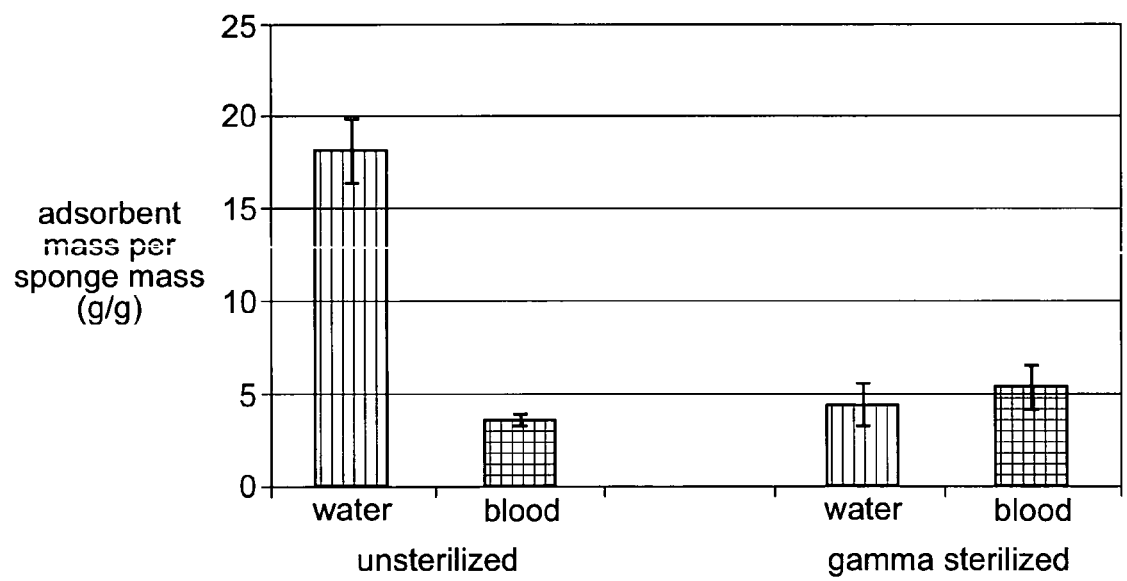

The average mass of medium adsorbed in 3 seconds per one gram of wound dressing was determined for gamma irradiated and un-irradiated chitosan samples (n=4) using blood or water as the wetting medium (see FIG. 11). The results were analyzed statistically using a one-way ANOVA with a Tukey-HSD test, p=0.001. Gamma irradiation significantly reduced the excessive adsorption of water in the case of the non-irradiated material. Such excessive water adsorption would cause wound dressing collapse (into a gel) with subsequent adhesive and structural failure.

Tensile test pieces of the chitosan dressings (Lot#OMLC_2SM114) were evaluated using a uniaxial Chatillon Materials Testing Vitrodyne V1000 equipped with a 5 kg load cell. Samples were cut into dog-bone pieces (15±1 mm×6.5±0.5 mm×5±0.5 mm gauge×thickness×width) and held between two clamps. The crosshead speed was 10 mm.s$^{-1}$. Load and displacement were recorded at 0.1 second intervals.

Tensile results are shown in Table 11. There were no significant differences between gamma irradiated and un-irradiated samples with respect to both stress and strain. There was a small increase in Youngs modulus with irradiation at 15 kGy.

TABLE 11

| Sample | Youngs Modulus (Mpa) | Ultimate Load* (kg) | Ultimate Elongation |
|---|---|---|---|
| No irradiation (n = 5) | 1.8 ± 1.2 | 2.2 ± 0.2 | 0.9 ± 0.1 |
| Gamma irradiation (n = 9) | 4.4 ± 2.7 | 2.3 ± 0.2 | 0.85 ± 0.15 |

*Calculated for a 2.5 cm wide bandage

Fifty two 4"×4" chitosan wound dressings (Lot#OMLC_2SM114) were prepared cleanly. Of these 4"×4" wound dressings, 46 were packaged in a double pack envelope and were sent to the IsoMedix facility in Ontario, Calif. for irradiation with gamma radiation at a certified dose between 14-15 kGy. Boxed with these samples were a set of 8 staphylococus aureus (ATCC 29213) doped chitosan wound dressing bars (1"×0.21"×0.21") cut from wound dressing 2SM114#1. Each bar was inoculated with 100 microliters of 0.5 MacFarlane inoculum. The staphylococcus aureus was swabbed from a demonstrably active control culture. A control set of 4 bars with no staphylococus was also included. Control samples with no gamma radiation treatment were kept in small sterile containers in heat sealed envelopes at room temperature and in the dark (see Table 12 for a summary of the controls).

TABLE 12

| Lot # | Control # | Pieces | Dosed | Gamma |
|---|---|---|---|---|
| OMLC_2SM114 | 61 | 4 | No | No |
| OMLC_2SM114 | 55 | 4 | No | No |
| OMLC_2SM114 | 65 | 4 | Yes | No |
| OMLC_2SM114 | 77 | 4 | Yes | No |
| OMLC_2SM114 | 74 | 4 | No | Yes |
| OMLC_2SM114 | 71 | 4 | Yes | Yes |
| OMLC_2SM114 | 58 | 4 | Yes | Yes |

The 46 irradiated wound dressing packages were opened under sterile conditions with sterile handling, an ethylene oxide sterile adhesive coated foam backing (3M 9781 tape) was attached, a small off-cut piece (ca. 1.2"×0.2×0.12") of each wound dressing and backing was removed for individual wound dressing sterilization testing and the wound dressings were repackaged inside the original inner pack by heat sealing. 40 of these wound dressings were labeled with lot number and wound dressing number and sent out for evaluation. The off-cut and control pieces were given to the microbiology facility at St Vincent's PHS for sterility testing.

The off-cut pieces and control pieces were placed aseptically in labeled sample vessels (0.6" diam.×5") containing enriched thioglycolate growth media and incubated aerobically at 35° C. The culture media were examined at 7, 14 and 21 days for indications of growth. The samples were subcultured in TSA W/5% sheep's blood, incubated at 35° C. and examined for growth after 48 hours.

The individual cultures were analyzed by turbidity testing and subculture swabbing. Absence of any growth in all the cultures and all the subcultures at 7, 14 and 21 days was demonstrated, even those cultures which were un-irradiated and dosed with staphylococcus aureus. Gram positive staining of particular cultures collaborated these findings.

The invention claimed is:

1. A method for producing a chitosan wound dressing comprising
   providing an aqueous solution including a chitosan biomaterial;
   placing the aqueous solution in a mold;
   freezing the aqueous solution within the mold by cooling the mold and aqueous solution according to prescribed conditions to form a frozen chitosan structure within the mold;
   removing water from the frozen chitosan structure by a prescribed freeze-drying process to form a sponge chitosan structure having a thickness and a density;
   compressing the sponge chitosan structure by the application of heat and pressure to reduce the thickness and increase the density of the sponge chitosan structure to form a densified chitosan structure; and
   preconditioning the densified chitosan structure by heating the densified chitosan structure according to prescribed conditions to form a wound dressing having adhesion strength and resistance to dissolution in high blood flow bleeding situations.

2. A method according to claim 1, further including degassing the aqueous solution before freezing the aqueous solution.

3. A method according to claim 1, wherein the application of heat and pressure during the compression comprises a compression temperature that is not less than about 60° C.

4. A method according to claim 1, wherein the prescribed conditions of preconditioning of the densified chitosan structure comprises heating the densified chitosan structure to a temperature of up to at least about 75° C.

5. A method according to claim 1, wherein the prescribed conditions of preconditioning of the densified chitosan structure comprises a period of time up to at least about 0.25 hours.

6. A method according to claim 1, wherein the application of heat and pressure during the compression comprises a compression temperature that is between about 60° C. to about 85° C.

7. A method according to claim 1, wherein the prescribed conditions of preconditioning of the densified chitosan structure comprises heating the densified chitosan structure to a temperature that is up to about 85° C.

8. A method according to claim 1, wherein the prescribed conditions of preconditioning of the densified chitosan structure comprises a period of time up to about 0.5 hours.

* * * * *